US009495488B2

(12) United States Patent
Jones et al.

(10) Patent No.: US 9,495,488 B2
(45) Date of Patent: Nov. 15, 2016

(54) METHOD FOR RECONSTRUCTING THE TOTAL ORGANIC CARBON CONTENT FROM COMPOSITIONAL MODELING ANALYSIS

(71) Applicant: Saudi Arabian Oil Company, Dhahran (SA)

(72) Inventors: Peter J. Jones, Dhahran (SA); Henry Ira Halpern, Pagsanjan (PH)

(73) Assignee: Saudi Arabian Oil Company, Dhahran (SA)

( * ) Notice: Subject to any disclaimer, the term of this patent is extended or adjusted under 35 U.S.C. 154(b) by 703 days.

(21) Appl. No.: 14/012,290

(22) Filed: Aug. 28, 2013

(65) Prior Publication Data

US 2014/0114627 A1    Apr. 24, 2014

Related U.S. Application Data

(60) Provisional application No. 61/694,037, filed on Aug. 28, 2012.

(51) Int. Cl.
*G06F 7/60* (2006.01)
*G06F 17/10* (2006.01)
*G06F 17/50* (2006.01)
*G01N 33/24* (2006.01)

(52) U.S. Cl.
CPC ........... *G06F 17/5009* (2013.01); *G01N 33/24* (2013.01)

(58) Field of Classification Search
CPC ............................. G06F 17/5009; G01N 33/24
USPC ............................................................. 703/2
See application file for complete search history.

(56) References Cited

U.S. PATENT DOCUMENTS

| 5,811,308 | A | 9/1998 | Espitalie et al. |
| 5,866,814 | A | 2/1999 | Jones et al. |
| 6,823,298 | B1 | 11/2004 | Jones et al. |
| 7,363,206 | B2 | 4/2008 | Jones et al. |
| 2010/0057409 | A1* | 3/2010 | Jones ............... G01N 33/24 703/2 |
| 2010/0161302 | A1* | 6/2010 | Walters ............ E21B 43/24 703/12 |

FOREIGN PATENT DOCUMENTS

WO    WO 2008/100614    8/2008

OTHER PUBLICATIONS

Peters, K.E., 1986, Guidelines for Evaluating Petroleum Source Rock Using Programmed Pyrolysis, Bulletin of the American Association of Petroleum Geologists, v. 70, p. 318-329.

Langford, F.F. and M.-M. Blank-Valleron, 1990, Interpreting Rock-Eval Pyrolysis Data Using Graphs of Pyrolizable Hydrocarbons vs. Total Organic Carbon, Bulletin of the American Association of Petroleum Geologists, v. 74, p. 799-804.

(Continued)

*Primary Examiner* — Dwin M Craig
(74) *Attorney, Agent, or Firm* — Abelman, Frayne & Schwab

(57) ABSTRACT

Methods are provided for utilizing the results of compositional modeling analysis to obtain accurate total organic carbon values without the need for an oxidation step or lengthy sample preparation, and also to calculate the organic carbon value attributable to contaminants, such as drilling additives.

7 Claims, 23 Drawing Sheets

(56) References Cited

OTHER PUBLICATIONS

Lafargue, E., J. Espitalié, F. Marquis, and D. Pillot, 2000, Rock-Eval 6 Applications in Hydrocarbon Exploration, Production, and in Soil Contamination Studies: Revue de L'institut Français du Pétrole, vol. 53, No. 4, p. 421-437.

Dahl, B., J. Bojesen-Koefoed, A. Holm, H. Justwan, E. Rasmussen, and E. Thomsen, 2004, A New Approach to Interpreting Rock-Eval S2 and TOC Data for Kerogen Quality Assessment, Organic Geochemistry, v. 35, pp. 1461-1477.

Jarvie 2012, in press, AAPG Memoir 97, Shale reservoirs—Giant resources for the 21st century, J. Breyer, ed., in press, Jarvie, Daniel M., 2012, Shale resource systems for oil and gas: Part 1—Shale gas resource systems; Part 2—Shale oil resource systems, AAPG Memoir 97, p. 69-119.

\* cited by examiner

FIG. 6
Prior Art

TABLE 1

| TITLE | Sample Report | | | | | | | |
|---|---|---|---|---|---|---|---|---|
| PROJECT | sample | | | | | | | |
| INSTRUM | POPI-1 | | | | | | | |
| OPERARTOR | | | | | | | | |
| WELL NAME | | | | | | | | |
| FILE NAME | C:\Program Files\POP\Data\UTMN1229\U1229_06.raw | | | | | | | |
| DEPTH | | | | | | | | |
| DATE | November 16 2002 | | | | | | | |
| TIME | ######## | | | | | | | |
| SEQUENCE | C:\Program Files\POP\Data\UTMN1229.pas | | | | | | | |
| ANALYSIS | C:\Program Files\POP\195630.PAR | | | | | | | |
| PROGRAM | NUM | ITEMP | ITIME | RATE | FTEMP | FTIME | | |
| PROGRAM | 1 | 195 | 3 | 25 | 630 | 0 | | |
| RESULT | SAMPLEN | SAMPLET | AMOUNT | LV | TD + TC | TMAX | TMIN | TD |
| RESULT | sample | SMP | 38.9 | 5.39362 | 12.95638 | 260.8579 | 400.1474 | 9.303264 |
| TC | TD/TC | LV+TD+TC | POPI | LV/TC+TD | API[S1/S2] | API[S1/S1+S2]@TMIN | | |
| 3.653116 | 2.546665 | 18.35 | 7.409852 | 0.416291 | 11.36505 | 30.73751 | | |
| DATA | SIGNAL | OVEN(°C) | TD + TC | Sum | Diff | | | |
| 0 | 574464 | 66.8 | | | | | | |
| 1 | 1264110 | 83 | | | | | | |
| 2 | 2772130 | 96.8 | | | | | | |
| 3 | 5664670 | 112.6 | | | | | | |
| 4 | 10013790 | 124.6 | | | | | | |
| 5 | 16174618 | 134.7 | | | | | | |
| 6 | 24601475 | 143.4 | | | | | | |
| 7 | 30782832 | 151 | | | | | | |
| 8 | 37969810 | 157.4 | | | | | | |
| 9 | 46847259 | 163.1 | | | | | | |
| 10 | 54391029 | 167.8 | | | | | | |
| DATA POINTS 11 TO 599 DELETED FOR BREVITY | | | | | | | | |
| 600 | 564035 | 610.8 | 405002.5 | 4.26E+09 | 405002.5 | | | |
| 601 | 561627 | 611.7 | 403273.5 | 4.26E+09 | 403273.5 | | | |
| 602 | 558608 | 612.6 | 401105.7 | 4.26E+09 | 401105.7 | | | |
| 603 | 556394 | 613.3 | 399515.9 | 4.26E+09 | 399515.9 | | | |
| 604 | 554090 | 614.1 | 397861.6 | 4.26E+09 | 397861.6 | | | |
| 605 | 551880 | 615 | 396274.7 | 4.26E+09 | 396274.7 | | | |
| 606 | 549402 | 615.7 | 394495.4 | 4.26E+09 | 394495.4 | | | |
| 607 | 547742 | 616.6 | 393303.4 | 4.26E+09 | 393303.4 | | | |
| 608 | 544603 | 617.4 | 391049.5 | 4.26E+09 | 391049.5 | | | |
| 609 | 542205 | 618.2 | 389327.6 | 4.26E+09 | 399327.6 | | | |
| 610 | 538718 | 619 | 386823.8 | 4.26E+09 | 386823.8 | | | |
| 611 | 536627 | 619.8 | 385322.3 | 4.26E+09 | 385322.3 | | | |

FIG. 12(a) Table 2: Calculation of $TOC_{RCN}$ for DBYT-1 Well

| End Member | $THI_{OM}$ | $OMHC_{Py}$ | $H/C_{OM}$ | $NOS_{EM}$ (wt. %) | $Wt\%H_{OM}$ | Inert Carbon |
|---|---|---|---|---|---|---|
| Free Oil | 1050 | 1.12 | 1.9 | 1.50% | 13.57% | 0.4 |
| Bitumen | 550 | 2.061 | 1.05 | 5.00% | 7.50% | |
| Kerogen | 300 | 3.699 | 0.65 | 5.00% | 4.64% | |

| DEPTH | Sample ID | Free Oil_YIELD (Yield$_{EMOil}$) | Free Oil Wt. OM (EM$_{Oil}$) Weight NSOs OM) | Free Oil Wt. NSOs (EM$_{Oil}$) Weight NSOs OM) | Free Oil Wt. H (EM$_{Oil}$) Weight H OM) | Free Oil Wt. %C (TOC$_{EMOil}$) | Bitumen_YIELD (Yield$_{EMBitumen}$) | Bitumen Wt. OM (EM$_{Bitumen}$) Weight OM) | Bitumen Wt. NSOs (EM$_{Bitumen}$) Weight NSOs OM) | Bitumen Wt. H (EM$_{Bitumen}$) Weight H OM) | Bitumen Wt. %C (TOC$_{EM}$ Bitumen) | Kerogen_YIELD (Yield$_{EMKerogen}$) | Kerogen Wt. OM (EM$_{Kerogen}$) Weight OM) | Kerogen Wt. NSOs (EM$_{Kerogen}$) Weight NSOs OM) | Kerogen Wt. H (EM$_{Kerogen}$) Weight H OM) | Kerogen Wt. %C (TOC$_{EM}$ Kerogen) | $TOC_{Inert}$ (wt. %) | $TOC_{RCN}$ | $TOC\_Inst$ (from Rock-Eval) | Delta $TOC_{RCN} - TOC_{Inst}$ |
|---|---|---|---|---|---|---|---|---|---|---|---|---|---|---|---|---|---|---|---|---|
| 10550.3 | DBYT1-001 | 2.178 | 2.439 | 0.037 | 0.331 | 0.207 | 2.5292 | 5.263 | 0.263 | 0.395 | 0.461 | 1.294 | 4.787 | 0.239 | 0.222 | 0.432 | 0.400 | 1.500 | 1.7 | 0.200 |
| 10552.2 | DBYT1-002 | 1.972 | 2.209 | 0.033 | 0.300 | 0.188 | 4.007 | 8.339 | 0.417 | 0.625 | 0.730 | 2.120 | 7.842 | 0.392 | 0.364 | 0.709 | 0.400 | 2.026 | 2.28 | 0.254 |
| 10554.7 | DBYT1-003 | 1.187 | 1.329 | 0.020 | 0.180 | 0.113 | 2.9057 | 6.047 | 0.302 | 0.454 | 0.529 | 0.708 | 2.618 | 0.131 | 0.122 | 0.237 | 0.400 | 1.279 | 1.47 | 0.191 |
| 10555.3 | DBYT1-004 | 5.053 | 5.659 | 0.085 | 0.768 | 0.481 | 7.9218 | 16.485 | 0.824 | 1.236 | 1.442 | 8.050 | 29.778 | 1.489 | 1.383 | 2.691 | 0.400 | 5.014 | 4.56 | -0.454 |
| 10557.7 | DBYT1-005 | 2.709 | 3.034 | 0.046 | 0.412 | 0.258 | 6.8929 | 14.344 | 0.717 | 1.076 | 1.255 | 2.215 | 8.194 | 0.410 | 0.380 | 0.740 | 0.400 | 2.653 | 3.11 | 0.457 |
| 10558.3 | DBYT1-006 | 1.837 | 2.057 | 0.031 | 0.279 | 0.175 | 3.806 | 7.920 | 0.396 | 0.594 | 0.693 | 0.161 | 0.595 | 0.030 | 0.028 | 0.054 | 0.400 | 1.322 | 1.35 | 0.028 |
| 10562.7 | DBYT1-007 | 1.532 | 1.715 | 0.026 | 0.233 | 0.146 | 0.8137 | 1.693 | 0.085 | 0.127 | 0.148 | 0.044 | 0.162 | 0.008 | 0.008 | 0.015 | 0.400 | 0.708 | 0.68 | -0.028 |
| 10567.8 | DBYT1-008 | 0.259 | 0.290 | 0.004 | 0.039 | 0.025 | 0.2251 | 0.468 | 0.023 | 0.035 | 0.041 | 0.123 | 0.453 | 0.023 | 0.021 | 0.041 | 0.400 | 0.507 | 0.34 | -0.167 |
| 10568 | DBYT1-009 | 0.467 | 0.523 | 0.008 | 0.071 | 0.044 | 0.4262 | 0.887 | 0.044 | 0.067 | 0.078 | 0.347 | 1.282 | 0.064 | 0.060 | 0.116 | 0.400 | 0.638 | 0.56 | -0.078 |
| 10572 | DBYT1-010 | 3.144 | 3.522 | 0.053 | 0.476 | 0.299 | 5.8799 | 12.236 | 0.612 | 0.918 | 1.071 | 3.472 | 12.844 | 0.642 | 0.599 | 1.161 | 0.400 | 2.930 | 3.03 | 0.100 |
| 10573 | DBYT1-011 | 0.180 | 0.201 | 0.003 | 0.027 | 0.017 | 0.2311 | 0.481 | 0.024 | 0.036 | 0.042 | 0.075 | 0.277 | 0.014 | 0.013 | 0.025 | 0.400 | 0.464 | 0.32 | -0.164 |
| 10575.2 | DBYT1-012 | 0.139 | 0.156 | 0.002 | 0.021 | 0.013 | 0.2473 | 0.515 | 0.026 | 0.039 | 0.045 | 0.090 | 0.333 | 0.017 | 0.015 | 0.030 | 0.400 | 0.488 | 1.02 | 0.532 |
| 10576.3 | DBYT1-013 | 0.855 | 0.958 | 0.014 | 0.130 | 0.081 | 1.4312 | 2.978 | 0.149 | 0.223 | 0.261 | 0.933 | 3.452 | 0.173 | 0.160 | 0.312 | 0.400 | 1.054 | 0.48 | -0.574 |
| 10579.3 | DBYT1-014 | 0.247 | 0.276 | 0.004 | 0.037 | 0.023 | 0.3557 | 0.740 | 0.037 | 0.056 | 0.065 | 0.235 | 0.870 | 0.044 | 0.040 | 0.079 | 0.400 | 0.607 | | |

To FIG 12(b)

FIG. 12(b) Table 2: Calculation of TOC$_{RCN}$ for DBYT-1 Well From FIG 12(a)

FIG. 13(a)   Replacement Table 2: Calculation of TOC$_{RCN}$ for Amad_2_Well

| End Member | THI$_{OM}$ | OM/HC$_{Py}$ | H/C$_{OM}$ | NOS$_{EM}$ (wt. %) | Wt%H$_{OM}$ | Inert Carbon |
|---|---|---|---|---|---|---|
| Free Oil | 1050 | 1.12 | 1.9 | 1.50% | 13.57% | 1.5 |
| Bitumen | 850 | 1.333 | 1.05 | 5.00% | 7.50% | |
| Kerogen | 800 | 1.425 | 0.65 | 5.00% | 4.64% | |

| DEPTH | Sample ID | Free_Oil_YIELD (Yield$_{EMOil}$) | Free Oil Wt. OM (EM$_{Oil}$) Weight OM) | Free Oil Wt. NSOs (EM$_{Oil}$) Weight NSOs OM) | Free Oil Wt. H (EM$_{Oil}$) Weight H OM) | Free Oil Wt. %C (TOC$_{EMOil}$) | Bitumen_YIELD (Yield$_{EMBitumen}$) | Bitumen Wt. OM (EM$_{Bitumen}$) Weight OM) | Bitumen Wt. NSOs (EM$_{Bitumen}$) Weight NSOs OM) | Bitumen Wt. H (EM$_{Bitumen}$) Weight H OM) | Bitumen Wt. %C (TOC$_{EM Bitumen}$) | Kerogen_YIELD (Yield$_{EMKerogen}$) | Kerogen Wt. OM (EM$_{Kerogen}$) Weight OM) | Kerogen Wt. NSOs (EM$_{Kerogen}$) Weight NSOs OM) | Kerogen Wt. H (EM$_{Kerogen}$) Weight H OM) | Kerogen Wt. %C (TOC$_{EM Kerogen}$) | TOC$_{inert}$ (wt. %) | TOC$_{RCN}$ | TOC_Inst (from Rock-Eval) | Delta TOC$_{RCN}$ - TOC$_{Inst}$ |
|---|---|---|---|---|---|---|---|---|---|---|---|---|---|---|---|---|---|---|---|---|
| 6160 | AMAD2-072 | 0.298 | 0.333 | 0.005 | 0.045 | 0.028 | 8.4659 | 11.736 | 0.587 | 0.880 | 1.027 | 9.347 | 13.319 | 0.666 | 0.618 | 1.204 | 1.500 | 3.759 | 4.69 | 0.931 |
| 6170 | AMAD2-073 | 0.000 | 0.000 | 0.000 | 0.000 | 0.000 | 3.2874 | 4.546 | 0.227 | 0.341 | 0.398 | 0.094 | 0.134 | 0.007 | 0.006 | 0.012 | 1.500 | 1.910 | 1.79 | -0.120 |
| 6180 | AMAD2-074 | 0.034 | 0.038 | 0.001 | 0.005 | 0.003 | 3.5776 | 4.948 | 0.247 | 0.371 | 0.433 | 0.837 | 1.192 | 0.060 | 0.055 | 0.108 | 1.500 | 2.044 | 2.1 | 0.056 |
| 6190 | AMAD2-075 | 0.174 | 0.195 | 0.003 | 0.027 | 0.017 | 4.6121 | 6.379 | 0.319 | 0.478 | 0.558 | 6.633 | 9.452 | 0.473 | 0.439 | 0.854 | 1.500 | 2.929 | 3.11 | 0.181 |
| 6200 | AMAD2-076 | 0.000 | 0.000 | 0.000 | 0.000 | 0.000 | 2.2593 | 3.125 | 0.156 | 0.234 | 0.273 | 0.000 | 0.000 | 0.000 | 0.000 | 0.000 | 1.500 | 1.773 | 1.59 | -0.183 |
| 6210 | AMAD2-077 | 0.085 | 0.095 | 0.001 | 0.013 | 0.008 | 3.5898 | 4.965 | 0.248 | 0.372 | 0.434 | 1.648 | 2.348 | 0.117 | 0.109 | 0.212 | 1.500 | 2.155 | 2.24 | 0.085 |
| 6220 | AMAD2-078 | 0.301 | 0.337 | 0.005 | 0.046 | 0.029 | 8.1279 | 11.241 | 0.562 | 0.843 | 0.984 | 13.218 | 18.835 | 0.942 | 0.875 | 1.702 | 1.500 | 4.214 | 4.49 | 0.276 |
| 6260 | AMAD2-079 | 0.762 | 0.853 | 0.013 | 0.116 | 0.072 | 2.1984 | 3.040 | 0.152 | 0.228 | 0.266 | 1.556 | 2.350 | 0.118 | 0.110 | 0.213 | 1.500 | 2.052 | 2.03 | -0.022 |
| 6330 | AMAD2-080 | 1.321 | 1.480 | 0.022 | 0.201 | 0.126 | 2.7745 | 3.837 | 0.192 | 0.288 | 0.336 | 0.000 | 0.000 | 0.000 | 0.000 | 0.000 | 1.500 | 1.961 | 1.42 | -0.541 |
| 7490.6 | AMAD2-039 | 0.049 | 0.055 | 0.001 | 0.007 | 0.005 | 1.1232 | 1.553 | 0.078 | 0.117 | 0.136 | 4.946 | 7.048 | 0.352 | 0.327 | 0.637 | 1.500 | 2.277 | 1.39 | -0.887 |
| 7491.6 | AMAD2-040 | 0.051 | 0.057 | 0.001 | 0.008 | 0.005 | 1.2475 | 1.725 | 0.086 | 0.129 | 0.151 | 3.906 | 5.565 | 0.278 | 0.258 | 0.503 | 1.500 | 2.159 | 1.78 | -0.379 |
| 7492.6 | AMAD2-041 | 0.874 | 0.979 | 0.015 | 0.133 | 0.083 | 1.2525 | 1.732 | 0.087 | 0.130 | 0.152 | 20.445 | 29.134 | 1.457 | 1.353 | 2.632 | 1.500 | 4.367 | 3.92 | -0.447 |
| 7497 | AMAD2-046 | 0.062 | 0.069 | 0.001 | 0.009 | 0.006 | 1.5139 | 2.094 | 0.105 | 0.157 | 0.183 | 5.961 | 8.494 | 0.425 | 0.394 | 0.767 | 1.500 | 2.457 | 2.06 | -0.397 |

To FIG 13(b)

FIG. 13(b) — From FIG 13(a)

| | | | | | | | | | | | | | | | | |
|---|---|---|---|---|---|---|---|---|---|---|---|---|---|---|---|---|
| 7488.5 AMMAG2-047 | 0.000 | 0.000 | 0.000 | 0.000 | 0.000 | 1.0612 | 1.468 | 0.073 | 0.110 | 0.128 | 3.603 | 5.142 | 0.257 | 0.239 | 0.466 | 1.590 | 2.093 | 1.63 | -0.473 |
| 7490.5 AMMAG2-048 | 0.000 | 0.000 | 0.000 | 0.000 | 0.000 | 0.9393 | 1.267 | 0.064 | 0.096 | 0.113 | 3.742 | 5.332 | 0.267 | 0.248 | 0.462 | 1.590 | 2.094 | 1.62 | -0.474 |
| 7492.5 AMMAG2-049 | 0.000 | 0.000 | 0.000 | 0.000 | 0.000 | 1.4214 | 1.966 | 0.096 | 0.147 | 0.172 | 3.710 | 5.536 | 0.264 | 0.245 | 0.478 | 1.590 | 2.150 | 1.64 | -0.510 |
| 7493.5 AMMAG2-050 | 0.000 | 0.000 | 0.000 | 0.000 | 0.000 | 1.2115 | 1.676 | 0.084 | 0.126 | 0.147 | 4.749 | 6.798 | 0.338 | 0.314 | 0.612 | 1.590 | 2.258 | 1.84 | -0.418 |
| 7500.5 AMMAG2-053 | 0.000 | 0.000 | 0.000 | 0.000 | 0.000 | 1.2679 | 1.754 | 0.088 | 0.132 | 0.153 | 0.000 | 0.000 | 0.000 | 0.009 | 0.000 | 1.590 | 1.653 | 1.41 | -0.243 |
| 7500.7 AMMAG2-051 | 0.047 | 0.053 | 0.001 | 0.004 | 0.004 | 1.375 | 1.902 | 0.095 | 0.143 | 0.166 | 5.833 | 8.320 | 0.416 | 0.386 | 0.752 | 1.590 | 2.423 | 1.82 | -0.603 |
| 7501.5 AMMAG2-052 | 0.078 | 0.085 | 0.001 | 0.012 | 0.007 | 2.3346 | 3.229 | 0.161 | 0.242 | 0.283 | 14.613 | 20.823 | 1.041 | 0.967 | 1.881 | 1.590 | 3.671 | 3.24 | -0.431 |
| 7502.5 AMMAG2-053 | 0.816 | 0.914 | 0.014 | 0.124 | 0.073 | 1.9225 | 2.202 | 0.110 | 0.165 | 0.193 | 26.235 | 37.366 | 1.699 | 1.738 | 3.378 | 1.590 | 5.148 | 4.46 | -0.088 |
| 7503.5 AMMAG2-054 | 0.378 | 0.414 | 0.008 | 0.058 | 0.035 | 4.0979 | 6.082 | 0.304 | 0.456 | 0.532 | 13.126 | 18.790 | 0.940 | 0.872 | 1.688 | 1.590 | 3.765 | 3.19 | -0.575 |
| 7505.5 AMMAG2-056 | 2.874 | 2.995 | 0.046 | 0.466 | 0.254 | 5.4913 | 7.594 | 0.380 | 0.570 | 0.665 | 35.166 | 50.111 | 2.306 | 2.327 | 4.528 | 1.590 | 6.947 | 5.72 | -1.227 |
| 7507.5 AMMAG2-057 | 2.361 | 2.531 | 0.035 | 0.316 | 0.193 | 3.195 | 4.419 | 0.221 | 0.331 | 0.387 | 23.507 | 33.498 | 1.675 | 1.555 | 3.027 | 1.590 | 5.111 | 4.59 | -0.521 |
| 7508.5 AMMAG2-058 | 0.364 | 0.407 | 0.006 | 0.085 | 0.035 | 5.8577 | 8.101 | 0.405 | 0.608 | 0.709 | 8.548 | 12.182 | 0.609 | 0.666 | 1.101 | 1.590 | 3.344 | 2.93 | -0.754 |
| 7509.5 AMMAG2-059 | 2.795 | 3.130 | 0.047 | 0.425 | 0.266 | 5.7395 | 7.938 | 0.397 | 0.595 | 0.695 | 37.447 | 53.352 | 2.668 | 2.473 | 4.822 | 1.590 | 7.282 | 6.26 | -1.022 |
| 7510.5 AMMAG2-061 | 0.392 | 0.439 | 0.007 | 0.060 | 0.037 | 8.0796 | 11.173 | 0.559 | 0.838 | 0.978 | 13.239 | 18.832 | 0.948 | 0.889 | 1.712 | 1.590 | 4.227 | 3.85 | -0.577 |
| 7511.5 AMMAG2-062 | 4.058 | 4.557 | 0.068 | 0.618 | 0.387 | 3.035 | 4.197 | 0.210 | 0.315 | 0.367 | 33.037 | 47.079 | 2.364 | 2.188 | 4.254 | 1.590 | 6.508 | 5.73 | -0.778 |
| 7512.5 AMMAG2-063 | 0.408 | 0.457 | 0.007 | 0.082 | 0.039 | 4.4139 | 6.104 | 0.305 | 0.458 | 0.534 | 14.487 | 20.643 | 1.032 | 0.953 | 1.865 | 1.590 | 3.938 | 3.33 | -0.606 |
| 7512.7 AMMAG2-064 | 0.902 | 1.010 | 0.013 | 0.137 | 0.056 | 5.5723 | 7.706 | 0.385 | 0.578 | 0.674 | 13.190 | 18.796 | 0.940 | 0.873 | 1.688 | 1.590 | 3.959 | 3.44 | -0.519 |
| 7513.5 AMMAG2-065 | 2.469 | 2.777 | 0.042 | 0.377 | 0.236 | 5.0413 | 6.978 | 0.349 | 0.523 | 0.610 | 41.494 | 59.129 | 2.966 | 2.745 | 5.343 | 1.590 | 7.795 | 7.40 | 0.155 |
| 7514.5 AMMAG2-066 | 1.968 | 2.204 | 0.033 | 0.293 | 0.187 | 2.5376 | 3.510 | 0.175 | 0.263 | 0.307 | 41.487 | 83.133 | 2.951 | 2.745 | 5.343 | 1.590 | 7.337 | 3.52 | -0.605 |
| 7515.5 AMMAG2-067 | 0.438 | 0.430 | 0.007 | 0.066 | 0.041 | 8.9297 | 12.346 | 0.617 | 0.928 | 1.090 | 11.672 | 16.633 | 0.832 | 0.772 | 1.503 | 1.590 | 4.123 | 5.26 | -0.481 |
| 7516.5 AMMAG2-068 | 3.517 | 3.939 | 0.059 | 0.535 | 0.335 | 5.0209 | 6.950 | 0.403 | 0.604 | 0.704 | 24.067 | 35.435 | 1.772 | 1.646 | 3.202 | 1.590 | 5.741 | 5.64 | -0.694 |
| 7516.5 AMMAG2-069 | 1.603 | 1.795 | 0.027 | 0.244 | 0.152 | 5.2539 | 7.266 | 0.363 | 0.545 | 0.636 | 31.190 | 44.446 | 2.222 | 2.064 | 4.016 | 1.590 | 6.304 | 5.64 | -0.673 |
| 7519.5 AMMAG2-070 | 2.465 | 2.763 | 0.042 | 0.378 | 0.236 | 8.0787 | 11.173 | 0.559 | 0.838 | 0.973 | 28.105 | 40.050 | 2.003 | 1.859 | 3.619 | 1.590 | 6.333 | 5.66 | -0.655 |
| 7520.5 AMMAG2-071 | 0.428 | 0.647 | 0.008 | 0.074 | 0.048 | 7.4745 | 10.337 | 0.517 | 0.775 | 0.905 | 7.851 | 11.331 | 0.567 | 0.526 | 1.024 | 1.590 | 3.475 | 2.79 | -0.655 |
| 7523.0 AMMAG2-095 | 0.559 | 0.603 | 0.009 | 0.082 | 0.051 | 4.6995 | 6.498 | 0.324 | 0.488 | 0.557 | 14.800 | 21.059 | 1.054 | 0.979 | 1.996 | 1.590 | 4.024 | 4.12 | 0.086 |
| 7523.0 AMMAG2-096 | 0.000 | 0.000 | 0.000 | 0.000 | 0.000 | 2.6853 | 3.726 | 0.186 | 0.268 | 0.326 | 0.840 | 1.197 | 0.060 | 0.056 | 0.108 | 1.590 | 1.934 | 1.86 | -0.074 |
| 7540.5 AMMAG2-096 | 0.199 | 0.223 | 0.003 | 0.030 | 0.019 | 5.2219 | 7.222 | 0.361 | 0.542 | 0.632 | 4.366 | 6.230 | 0.312 | 0.299 | 0.565 | 1.590 | 2.716 | 2.44 | -0.275 |
| 7550.5 AMMAG2-097 | 0.000 | 0.000 | 0.000 | 0.000 | 0.000 | 2.0191 | 2.792 | 0.140 | 0.209 | 0.244 | 0.009 | 0.013 | 0.001 | 0.001 | 0.001 | 1.590 | 1.745 | 1.55 | -0.195 |
| 7570.5 AMMAG2-099 | 0.000 | 0.000 | 0.000 | 0.000 | 0.000 | 2.0429 | 2.825 | 0.141 | 0.212 | 0.247 | 0.009 | 0.008 | 0.000 | 0.000 | 0.000 | 1.590 | 1.747 | 1.55 | -0.197 |

METHOD FOR RECONSTRUCTING THE TOTAL ORGANIC CARBON CONTENT FROM COMPOSITIONAL MODELING ANALYSIS

FIELD OF THE INVENTION

The present invention relates to a method for reconstructing the total organic carbon (TOC) values in geological samples by a combination of pyrolysis, chemical analysis, and compositional modeling in order to determine the quality of unconventional oil resources or source rocks for use during development drilling and/or exploration operations.

BACKGROUND OF THE INVENTION

The use of open system pyrolysis, as used in the commercial Rock Eval™ analysis, and total organic carbon measurement employed by the Rock Eval™ and LECO™ analysis systems are methods that have long been used in the assessment of petroleum source rocks. See, e.g., Peters, K. E., 1986, Guidelines for Evaluating Petroleum Source Rock Using Programmed Pyrolysis, Bulletin of the American Association of Petroleum Geologists, v. 70, p. 318-329; U.S. Pat. No. 5,811,308, Expitalie et al., Method for Determining Petroleum Characteristics of Geologic Sediments Sep. 22, 1998; Langford, F. F. and M.-M. Blank-Valleron, 1990, Interpreting Rock-Eval Pyrolysis Data Using Graphs of Pyrolizable Hydrocarbons vs. Total Organic Carbon, Bulletin of the American Association of Petroleum Geologists, v. 74, p. 799-804; Lafargue, E., J. Expitalié, F. Marquis, and D. Pillot, 2000, Rock-Eval 6 Applications in Hydrocarbon Exploration, Production, and in Soil Contamination Studies: Revue de L'institut Francais du Parole, Vol. 53, No, 4, p. 421-437. These methods, however, rely on bulk measurements of all organic matter present in a sample and can only provide information from empirically-derived cutoff values and parameters. Methods and systems described in U.S. Pat. No. 7,363,206 and WO 2008/100614 (PCT/US2008/002102) demonstrate that pyrolysis data can be used to characterize the relative amounts of organic matter and contaminants in geological samples.

The Pyrolytic Oil-Productivity Index (POPI) technology originally disclosed in U.S. Pat. No. 5,866,814 has been used successfully in exploration and development wells to quickly and accurately assess the reservoir rock for tar mats and other types of organic matter as the drilling progresses through these layers in the reservoir rock. The POPI method has been incorporated in the commercially available software program identified as GC-ROX™ which is an acronym for "Geochemical Residual Oil eXpert-modeling". The GC-ROX™ program can be used to optimize oil field development by tar mat identification and quantification, and can be used to validate, organize and store field-data. Earlier observations from various field data had suggested a cut-off of productivity exists at about 3% tar. However, relying on the more precise information produced by the GC-ROX software, a target of 1% tar has been used commercially for injectivity purposes. Interest has been shown in linking the POPI method and information to viscosity. It is thought that proxies could be developed, but the main application of the technique is identification and quantification of tar.

The process of petroleum source rock maturation and hydrocarbon generation is well understood, with the effects of burial and temperature causing kerogen to break down into bitumen, free oil that is expelled and migrates, and eventually into gas. Methods using compositional modeling are disclosed in U.S. Pat. No. 7,363,206 which permit the user to identify the relative proportions by percent of a plurality of end member components in a sample of reservoir rock. This methodology represented a significant advance in the art, since prior methods only provided bulk values or parameters.

The compositional modeling method for assessing residual hydrocarbon staining that is taught in U.S. Pat. No. 7,363,206 at column 6, line 56 to column 9, line 48, is preferred for use in the present invention. As used herein and specifically in the claims, the term "compositional modeling" shall mean the method disclosed in U.S. Pat. No. 7,363,206 and as described below. The disclosure of U.S. Pat. No. 7,363,206 is incorporated herein by reference.

These factors are: (1) the amount of total hydrocarbon yield, and (2) the similarity of the hydrocarbon staining to the produced oils. Pyrolysis instruments are useful for quantifying the amount of hydrocarbon staining and the POPI method assesses the similarity to produced oils by subdividing the hydrocarbons into the Light Volatile (LV), Thermally Distillable (TD), and Thermally Crackable (TC) components (FIG. 1). However, it has been discovered that visual inspection of pyrograms also can be useful in assessing the type of hydrocarbons present because oil, tar, pyrobitumen, and other typical organic matter each also have very characteristic appearances.

FIGS. 2a through 2d are examples of pyrograms for samples with a nearly uniform composition of specific hydrocarbon or pyrolytically identifiable type of organic matter end-member components. These plots show the hydrocarbon yield on the y-axis for each data step that is recorded on the x-axis.

The number of data steps for a particular analysis can vary based on the type of pyrolyis instrument used. Two such commercially available instruments are Vinci's ROCK-EVAL™ and Humble's SOURCE ROCK ANALYZER™. The data that is obtained from the instrument and converted into a digital file can also vary. In the case description and examples that follow, the SOURCE ROCK ANALYZER™ was used and the data were output into digital form using a MICROSOFT EXCEL™ CSV file that recorded the yield and temperature over 611 data steps. The first 111 steps record the isothermal hold at 195 degrees C. for 3 minutes and the next 500 steps record the programmed temperature run from 195 degrees C. to 630 degrees C. In general, the temperature associated with any specific step is the same from run to run, so that the step number can be associated with the temperature of the oven during the run.

Compositional modeling for a sample includes entering in an appropriately programmed computer the yield at each individual data step as a value that is made up of the aggregate yield of the various end-member components. In this method, a specific and consistent temperature is associated with each step. The difference between the modeled yield calculated in accordance with the algorithm from the theoretical end-member component or components and the actual yield provides the basis for assessing whether a particular solution accurately reflects the actual composition in the reservoir rock sample.

Each such solution that is assessed must sum the difference between the calculated yield and the actual yield over all the data steps for the sample. Any of a number of statistical methods can be used in quantifying the overall error for any proposed solution. The modeling relies on iteratively varying the concentration of the various components until the aggregate error is minimized and the curves appear very similar. In one preferred embodiment, the software utilizes the iterative process of proposing different compositions, calculating a hypothetical curve based on the yield at each data step, assessing the error for each particular solution, and then minimizing this aggregate error. These method steps can advantageously be completed by the use of macros and the Solver add-on application that is a standard component of the Microsoft Excel™ program, and its use greatly automates and expedites the process. There are other software packages that can also be utilized to facilitate the methods used to model hydrocarbon composition that are commercially available and include Corel Quattro Pro, Lotus 1-2-3, Corel Paradox, Lotus Approach, Microsoft Access and Microsoft Visual FoxPro.

Table 1, shown in FIG. 6, is the output file from a Humble SOURCE ROCK ANALYZER™ that has been converted to CSV format. The output data file records the same information in the same location for each sample tested and facilitates its extraction by spreadsheet data analysis programs. The header information at the very top of the report records the calculated parameters from the instrument and the run parameters. Starting at row 22, the instrument records the curve signal in the first three columns of the file. The first column contains the data step number, the second column records the signal from the flame ionization detector (FID) in milliVolts (mV), and the third column records the temperature of the oven associated with the data step.

In order to convert the output of the instrument into hydrocarbon yield using the instrument software, a known standard compound or composition from the reservoir region is analyzed. With the data from the standard, the instrument can calculate the conversion factor (CF) to relate millivolts from the FID to hydrocarbon yield in units of milligrams per gram of rock (g Rock). From the data file, these conversion factors are calculated for each sample by summing the total signal in column two and then dividing this signal by the total hydrocarbon yield of the sample in accordance with the following mathematical expression:

$$CF_{FID} = [\Sigma Signal_{step\ 1-611}\ (mV)]/[(LV+TD+TC)\ (mgHC/g\ Rock)] \quad (1)$$

The signal that is taken for any particular data step is then be converted into mgHC/gRock by simply dividing the signal by CF:

$$Yield_{step\ X}\ (mgHC/g\ Rock) = [Signal_{STEP\ X}\ (mV)]/[CF_{FID}\ (mV/mgHC/g\ ROCK)] \quad (2)$$

In a preferred embodiment, all instrument output is converted into yields for the purpose of making the relevant calculations to combine end-members (EM) and to compute the results based on modeled solutions. This is done because the actual yield that is given for each end-member sample and for each sample that is being modeled will be unique. In order to model the relative composition of end-members that make up a particular sample, the data for each end-member is normalized so that the total hydrocarbon yields of each recalculated end-member is the same as the actual sample. Therefore, the quantity of an end-member component that would be present for a pure end-member having the same yield as the sample can be expressed as follows:

$$Yield = [Yield_{EMSTEPX}] * ([Total\ Yield(THC)Sample]/[Total\ Yield\ End\text{-}Member]) \quad (3)$$

In the above equation (3) and those that follow the "*" notation is used to indicate multiplication.

Equation (3) is used to calculate the aggregate yield that would be found for a hypothetical sample that contained various percentages of end-members that are needed to describe the sample behavior. Thus, the calculated yield for a proposed hydrocarbon composition at any given data step is the sum of the percentages of each end-member (% $EM_{1\ to\ 5}$) divided by 100 and multiplied by the yield of the end-member at step x ($Yield_{EM1\ to\ 5,X}$) times the ratio of the total yield of the sample divided by the total yield of the end-member ($THC_{sample}/THC_{EM1\ to\ 5}$). This step can be expressed as follows:

$$\begin{aligned} \text{Calculated } Yield_{EM\ 1-5,X} = \quad & (4) \\ (\% EM_1/100) * Yield_{EM1,X} * (THC_{sample}/THC_{EM1}) + \\ (\% EM_2/100) * Yield_{EM2,X} * (THC_{sample}/THC_{EM2}) + \\ (\% M_3/100) * Yield_{EM3,X} * (THC_{sample}/THC_{EM3}) + \\ (\% EM_4/100) * Yield_{EM4,X} * (THC_{sample}/THC_{EM4}) + \\ (\% EM_5/100) * Yield_{EM5,X} * (THC_{sample}/THC_{EM5}) \end{aligned}$$

The error between a particular modeled solution for Step X and the actual analytical result for Step X can be obtained by simple difference. However, since some of these values will be positive and some negative, the treatment of errors for all values calculated, e.g., Steps 1-611, is easier to accomplish through the application of a root mean squares (RMS) calculation. Other statistical treatments can be used to also achieve the same results if they employ the difference between each modeled yield and actual yield as an absolute value.

In one preferred method, the RMS average difference is calculated in terms of a percentage that relates to the total response of the sample and can be expressed as follows:

$$\%RMS_{CALC\ vs\ ACTUAL} = 100 * ((AVERAGE_{STEP,\ 1-611}(Yield_{CALC} - Yield_{ACTUAL})^2)^{1/2} / (AVERAGE_{STEP,\ 1-611}(Yield_{ACTUAL}))) \quad (5)$$

The modeling process comprises the steps of varying the percentage of the end-members that are present in the system in which ($EM_{1-5}$ are preferably used) until the calculated curve matches the actual curve and the % RMS error is minimized. Due to the fact that so many calculations must be made to assess any solution, the use of a spreadsheet program to perform these calculations and automatically plot the result that is achieved greatly simplifies the process. Moreover, a software application such as Solver that is present as an add-on in Microsoft Excel™, can greatly expedite the data processing capability of iteratively solving problems with multiple variables that seek to converge on a desired solution which in this case is minimizing error.

FIG. 3 shows the graphic interface that was utilized for a five end-member component system at well-site Z. The graphic illustration includes curves for the current sample, the calculated solution based on the percentage of the components, the oil end-member, the tar end-member, the shale end-member (typical of dispersed kerogen found in shaley lithologies), the coal end-member, and the drilling mud end-member (contamination). The parameter listed on the top line as $DEV_{RM}$ is the RMS deviation as a percent of total yield and is the value that is minimized in obtaining a reasonable solution for a given sample. When all samples are analyzed for a particular well, the results can be plotted as in FIG. 4 to reveal how the composition varies throughout the sampled section. The numerical references 1-4 on the graph are to the legends at the top. Plots such as these are very useful in identifying important trends, such as increasing tar, or in identifying individual coal or tar units that may have important implications in reservoir performance. An alternative method of presenting the data as is shown in FIG. 5, is to plot the relative contribution of each EM component by depth with each curve being adjusted for changes in yield in the samples. This type of plot is particularly useful for identifying true tar mats that typically have an associated dramatic increase in hydrocarbon yield as opposed to a change in composition that appears to be tar, but is present in relatively low concentrations and not likely to affect reservoir performance.

As used herein, it will be understood from the description that "compositional modeling" includes the following steps:
 a. identifying the end-member components known to be present in reservoir rock in the oil field;
 b. preparing individual pyrograms consisting of a pcd for each of the components identified in step (a);
 c. storing the pcd for each component in a digital data file;
 d. conducting a pyrolytic analysis of a sample from the oil field of reservoir rock that contains one or more hydrocarbon and organic matter components of the type identified in step (a) to obtain pcd for the sample;
 e. comparing the pcd for the sample with the pcd obtained in step (b) for each of the components, measuring and recording the difference between the sample pcd and the pcd for each of the components;
 f. applying a statistical analysis to minimize the aggregate differences between the pcd for the sample and a combination of pcd selected from the components;
 g. recording for retention and display for analysis the resulting pcd that constitutes the minimum aggregate error over the temperature range of the pyrolytic analysis; and
 h. analyzing the displayed data to identify the respective components.

As used herein, "unconventional oil" and "unconventional oil sources" include oil shales; organic-rich fine-grained carbonates, low-porosity low-permeability sandstones/siltstones/carbonates that are adjacent to hydrocarbon source units; oil sands, and heavy crude oils. Unconventional oil reservoirs are often source rocks that are being exploited to produce hydrocarbons that were unable to migrate as in conventional hydrocarbon reservoirs. One problem faced by geoscientists is how to classify the organic matter and hydrocarbon components at specific depths and/or intervals in the well, since it is recognized that such information, if available, would be extremely useful in assessing the reservoir during exploration and development drilling.

Knowledge of the quantity and types of organic matter and hydrocarbons present in unconventional reservoirs is critical to well performance evaluation and geochemical methods are used to provide this information. Traditional petrophysical analysis focuses principally on the rock matrix; however, the storage and flow capacity of unconventional reservoirs is highly dependent on the organic porosity resulting from the transformation of kerogen. Although total organic carbon (TOC) values are important to reservoir evaluation and assessment, traditional TOC measurement is not available at the well site in real-time in order to meaningfully assist in optimizing drilling operations.

The prior art methods require either time-consuming sample processing, such as the demineralization needed for the LECO™ analyzer, e.g., the LECO (EC 12) carbon analyzer; and preparation of samples using the TOC measurement or they require long analytical times by more complex instrumentation that is not suitable for use at well drilling sites where the rock samples are recovered from the drilling fluid. In addition, the prior art methods are bulk analytical methods which do not differentiate between the materials present in mixtures.

A new method that can be deployed at the well site to provide information that can be used to guide the drilling operation for exploratory and development wells is needed.

Definitions

As used herein, it is to be understood that the following terms and designations have the meanings indicated:

Bitumen—generally refers to the organic material that is extractable through the use of organic solvents and encompasses those obtained through the use of strong organic solvents such as methylene chloride, chloroform, and toluene.

End Member (EM)—A consistent type of organic matter or hydrocarbon that can be distinguished by pyrolytic analysis. End members include oil, soluble tar, pyrobitumen (insoluble tar), kerogen, coal, drilling mud and other contaminants. Specific end members are associated with specific fields and reservoirs. A reference to "local" end members means end members that have been determined to be present in the field and/or nearby wells based on analysis and examination of core samples, well logs, and drilling rock samples, also referred to below as "comparative samples".

$EM_x$ Weight OM—the weight attributable to the organic matter (in milligrams per gram of rock) of one component end member (x) in a sample.

$EM_x$ Weight NSOs OM—the weight attributable to the elemental nitrogen, sulfur, and oxygen content (in milligrams per gram of rock) of one component end member (x) in a sample.

$EM_x$ Weight H—the weight attributable to the elemental hydrogen content (in milligrams per gram of rock) of one component end member (x) in a sample.

FID—Flame Ionization Detector

Free Oil—hydrocarbons that have been generated through the maturation of kerogen that are similar to producible oil and may be expelled from a source rock given a sufficient saturation level.

HC—Abbreviation for hydrocarbons, THC is used for Total Hydrocarbons.

$H/C_{OM}$—the ratio of hydrogen to carbon in the organic matter of an end member component.

Inert Carbon—Organic Carbon, that can be oxidized to $CO_2$ and CO by application of heat as in traditional source rock analysis in the oxidation cycle or by LECO carbon analyzer, but that cannot be liberated by pyrolysis in an inert atmosphere either due to character of the organic matter or the adsorptive properties of the mineral matrix.

Kerogen—the product of biochemical degradation, polycondensation, insolubilization of biologically-derived material due to burial, time and temperature.

LV—Abbreviation for light volatile components. As used herein, LV refers specifically to the weight in milligrams of HC released per gram of rock at the initial static temperature condition of 180° C. (when the crucible containing the rock sample is inserted into the pyrolytic chamber) prior to the temperature-programmed pyrolysis of the sample.

Non-Pyrolizable Hydrocarbons ($HC_{Non-py}$)—compounds composed primarily of carbon and hydrogen that cannot be liberated through evaporation or decomposition of organic material during pyrolysis and require combustion to analyze the different elemental components.

$NOS_x$%—the weight percent of Nitrogen, Oxygen, and Sulfur in the organic matter of an end member component.

Organic Matter (OM)—generally biologically produced materials that are composed primarily of carbon and hydrogen, such as shale- and coal-like materials.

OM/HC$_{py}$—the ratio of organic matter to pyrolizable hydrocarbons in an end member component.

POPI—Abbreviation for the Pyrolytic Oil-Productivity Index. The POPI is calculated from the pyrolytic data by the following equation: POPI=ln(LV+TD+TC)×(TD/TC), where ln is the logarithmic value and TD and TC are as defined below.

Pyrolizable Hydrocarbons (HC$_{py}$)—compounds composed primarily of carbon and hydrogen that can be liberated through evaporation or decomposition of organic material in response to the application of heat in an inert atmosphere (i.e., not containing oxygen).

Pyrolytic Characterization Data (pcd)—Data values measured at a predetermined number of data points, each data point corresponding to a prescribed temperature.

Rock-Eval™ S1 Yield—weight in milligrams of HC released per gram of rock at the initial static temperature condition of 300° C. of a standard Rock-Eval™ pyrolysis analysis as described in Peters, K. E., 1986, Guidelines for Evaluating Petroleum Source Rock Using Programmed Pyrolysis, Bulletin of the American Association of Petroleum Geologists, v. 70, p. 318-329.

Rock-Eval™ S2 Yield—weight in milligrams of HC released per gram of rock during the programmed pyrolysis portion of a standard Rock-Eval analysis, where the temperature is raised from 300° C. to 550-600° C. at a rate of 25° C./minute, as described in Peters, K. E., 1986, Guidelines for Evaluating Petroleum Source Rock Using Programmed Pyrolysis, Bulletin of the American Association of Petroleum Geologists, v. 70, p. 318-329.

Source Rock—A sedimentary rock, deposited in a low-energy environment, generally of fine-grained nature (i.e., composed of silt and clay-sized particles), typically fissile, commonly composed of silica, clay, and carbonate minerals, and with sufficient organic matter content and quality to generate and expel hydrocarbons (i.e., petroleum).

TD—Abbreviation for "thermally distillable" components that, as used herein, refers specifically to the weight in milligrams of HC released per gram of rock at a temperature between 180° C. (195° C. on a Humble SR Analyzer) and T$_{min}$(° C.).

TC—Abbreviation for "thermally crackable" components that as used herein, refers specifically to the weight in milligrams of HC released per gram of rock at a temperature between T$_{min}$(° C.) and 600° C. (630° C. on a Humble SR Analyzer).

THC—Abbreviation for total hydrocarbons.

T$_{min}$—The temperature at which the hydrocarbon yield, as measured by a flame ionization detector (FID) during pyrolysis employing the POPI method, reaches a minima between the peaks representing the thermally distilled and thermally cracked hydrocarbon peaks, generally occurring between 380° C. and 420° C.

Total Hydrocarbon Index (THI)—Represents the total HC released, including during the initial heating and programmed pyrolysis from 195° C. and 630° C., relative to Total Organic Carbon in a sample. The equation for calculating THI is: THI=[(LV+TD+TC)/TOC]×100.

THI$_{OM}$—the Total Hydrocarbon Index of organic matter in an end member component.

Total Organic Carbon (TOC)—The TOC is the weight percent of organic carbon found in a rock sample.

TOC$_{EMx}$ [%]—The total organic carbon in weight percent that is attributable to a specific end member. This is found by taking total weight of the organic matter represented by the end member (EM$_x$ Weight OM), subtracting the weight of the end member attributable to elemental Nitrogen, Sulfur, and Oxygen (EMx Weight NSOs), subtracting the weight of the end member attributable to elemental hydrogen (EMx Weight H), then converting it to a decimal by dividing by 1000 mg/g Rock, and finally multiplying by 100 to put the number into percent form.

TOC$_{inert}$—The portion of total organic carbon in weight percent that cannot be decomposed and detected by pyrolysis, but requires measurement of carbon dioxide and monoxide produced during an oxidation step at high temperature.

TOC$_{RCN}$—The reconstructed total organic carbon, which is not directly measured, but rather by summing the TOC for each end member and the inert carbon present in the sample (also known as, TOC$_{CoMod}$) as follows: TOC$_{RCN}$=TOC$_{EM1}$+TOC$_{EM2}$ . . . . TOC$_{EMx}$+TOC$_{inert}$.

Wt % H$_{OM}$—the weight percent of Hydrogen in the organic matter as determined by CHNOS elemental analysis.

Yield$_{EMx}$—the hydrocarbon yield (in milligrams of hydrocarbon per gram of rock) that is attributable to each end member from applying compositional modeling as described in U.S. Pat. No. 7,363,206.

SUMMARY OF THE INVENTION

In accordance with the present invention, a method is provided for utilizing the results from compositional modeling analysis to provide accurate total organic carbon (TOC) data for assessment without the need for either an oxidation step or lengthy sample preparation as required by LECO TOC apparatus and method. The present method utilizes nonobvious procedures to assess the level of inert carbon present in geological reservoir rock samples and identifies and quantifies differences in the amount of pyrolizable hydrocarbons related to the geological maturity of the sample. The method of the invention also accounts for the presence of organic carbon attributable to known contaminants, such as drilling additives, which can include a large variety.

The associated methods of the present invention are unique because they allow the determination of total organic carbon in geological samples without time-consuming steps for sample preparation, do not subject the sample to combustion, and only require a flame ionization detector (FID). The methods provide superior assessment of the types of organic matter present in samples and also indicate the presence of mobile hydrocarbons.

Although other workers have noted the contribution of different materials present in geological samples to be analyzed for total organic carbon, all of these prior art methods rely on simple bulk measurements of the materials. Because the method of the present invention provides a detailed assessment of the organic materials found in a rock sample, a unique understanding of the organic matter transformation process is also achieved by this new method. None of the prior art methods can provide a detailed picture in the form of a graphic display of the organic matter contributing to the total organic carbon value from a rock sample.

The method includes the following steps:
a. collecting a plurality of representative rock samples typical of unconventional oil reservoirs and source rocks;
b. performing pyrolytic analysis on the rock samples in accordance with the POPI method(s), as described in U.S. Pat. No. 5,866,814;

c. obtaining and reviewing the pyrolysis data for samples from a reservoir to assess the likely end-member components that appear to be present;
d. selecting samples that appear to have a nearly uniform composition of a particular end-member, that is, those appearing to be composed mostly of one member, e.g., "free oil", bitumen, kerogen, or the like, based upon an inspection of the pyrolysis curve or by a visual inspection of the sample by experienced technical or engineering personnel;
e. performing separation from the rock sample of any moveable hydrocarbon components by extraction with a non-polar solvent, e.g., cyclohexane, and saving both the solvent extract and the extracted rock;
f. performing separation of soluble tar from the extracted rock sample by extraction with a strong organic solvent (e.g., methylene chloride), saving both the solvent extract and the extracted rock;
g. performing separation of residual organic matter on a portion of the strong organic solvent-extracted rock sample by demineralization methods;
h. analyzing all extracts and organic matter separations by elemental analysis to determine the percent of C, H, N, O and S in each sample;
i. analyzing all solvent extracts, extracted rock samples, and separated organic matter by the pyrolysis-TOC method to determine the total hydrocarbon index (THI) in accordance with prior art method(s), as described in WO 2008/100614 or US 2010/0057409 A1;
j. analyzing the pyrolysis data using the prior art compositional modeling method, as described in U.S. Pat. No. 7,363,206;
k. recording the results for the percentage of total yield for end-members for the group of samples;
l. employing prior art methods, as described in WO 2008/100614 or US 2010/0057409 A1 to obtain parameters for the total hydrogen index ($THI_{OM}$), the ratio of organic matter to pyrolizable hydrocarbons ($OM/HC_{py}$), the ratio of hydrogen to carbon in the organic matter ($H/C_{OM}$), the percent of Nitrogen, Oxygen, and Sulfur in the organic matter ($NOS_x\%$), and the weight of Hydrogen in the organic matter (Wt % $H_{OM}$);
m. analyzing a plurality of samples from a well that has a source rock or unconventional reservoir for which the reconstructed TOC values are needed;
n. applying the compositional modeling method described in U.S. Pat. No. 7,363,206 to obtain the hydrocarbon yield attributable to each end member ($Yield_{EMx}$) in a group of samples from the source rock or unconventional reservoir;
o. determining the weight of organic matter represented by the hydrocarbon yield by applying the equation: $EM_x$ Weight OM=$Yield_{EMx}*OM/HC_{py}$;
p. determining the weight of elemental nitrogen, sulfur and oxygen by the equation: $EM_x$ Weight NSOs=$NOS_x\%*EM_x$ Weight OM;
q. determining weight of Hydrogen for each end member in a sample by the equation: $EM_x$ Weight H=Wt % $H_{OM}*EM_x$ Weight OM;
r. calculating the total organic carbon for the end member ($TOC_{EMx}$) as follows: $TOC_{EMx}$=($EM_x$ Weight OM–$EM_x$ Weight NSOs–$EM_x$ Weight H)×100/1000 mg/g Rock; and
s. summing the TOC for each end member and the inert carbon present in the formation to obtain the value of reconstructed total organic carbon ($TOC_{RCN}$ or $TOC_{CoMod}$) as follows: $TOC_{RCN}=TOC_{EM1}+TOC_{EM2}\ldots TOC_{EMx}+TOC_{inert}$.

The reconstruction of the TOC measurement from compositional modeling in accordance with the above method requires significantly less analytical time to produce data for decision making than the methods of the prior art. Consequently, the results are produced with greater frequency to assist with the identification of potentially productive reservoir intervals. Also, because the individual organic materials present within the rock sample can be differentiated, including organic contaminants from the drilling mud, the results can be corrected to include only TOC that is indigenous to the rocks that have been produced during the drilling of the well.

BRIEF DESCRIPTION OF THE DRAWINGS

The invention will be described in further detail below and with reference to the attached drawings in which:

FIGS. 1-5 are representative of prior art graphic plots, and specifically:

FIG. 1 is a typical output pyrogram from an instrument performing open-system temperature programmed pyrolysis;

FIG. 3 is a plot showing the compositional modeling interface that was developed to perform the calculations, where the plot shows pyrograms associated with the current sample, the calculated solution and the end-members that are used in the modeling process;

FIG. 4 is the resultant compositional modeling for well Z-95 showing the percentage of oil, tar, shaley OM and coal present in reservoir rock samples;

FIG. 5 is the plot resulting from the compositional modeling of well Z-95 showing the relative pyrolytic yield of oil, tar, shaley OM and coal present in reservoir rock samples and demonstrates how hydrocarbon yield increases significantly in true tar mats or coal beds;

FIG. 6, which is referred to in the specification as Table 1, is an illustrative representative reproduction for a hypothetical sample of the output file of a commercial pyrolysis instrument;

FIGS. 12A-B, which is referred to in the specification as Table 2, is a calculation of $TOC_{RCN}$ for well DBYT-1;

FIGS. 13A-B, which is referred to in the specification as Table 3, is a calculation of $TOC_{RCN}$ for well Amad_2;

DETAILED DESCRIPTION OF THE INVENTION

Figure 1:
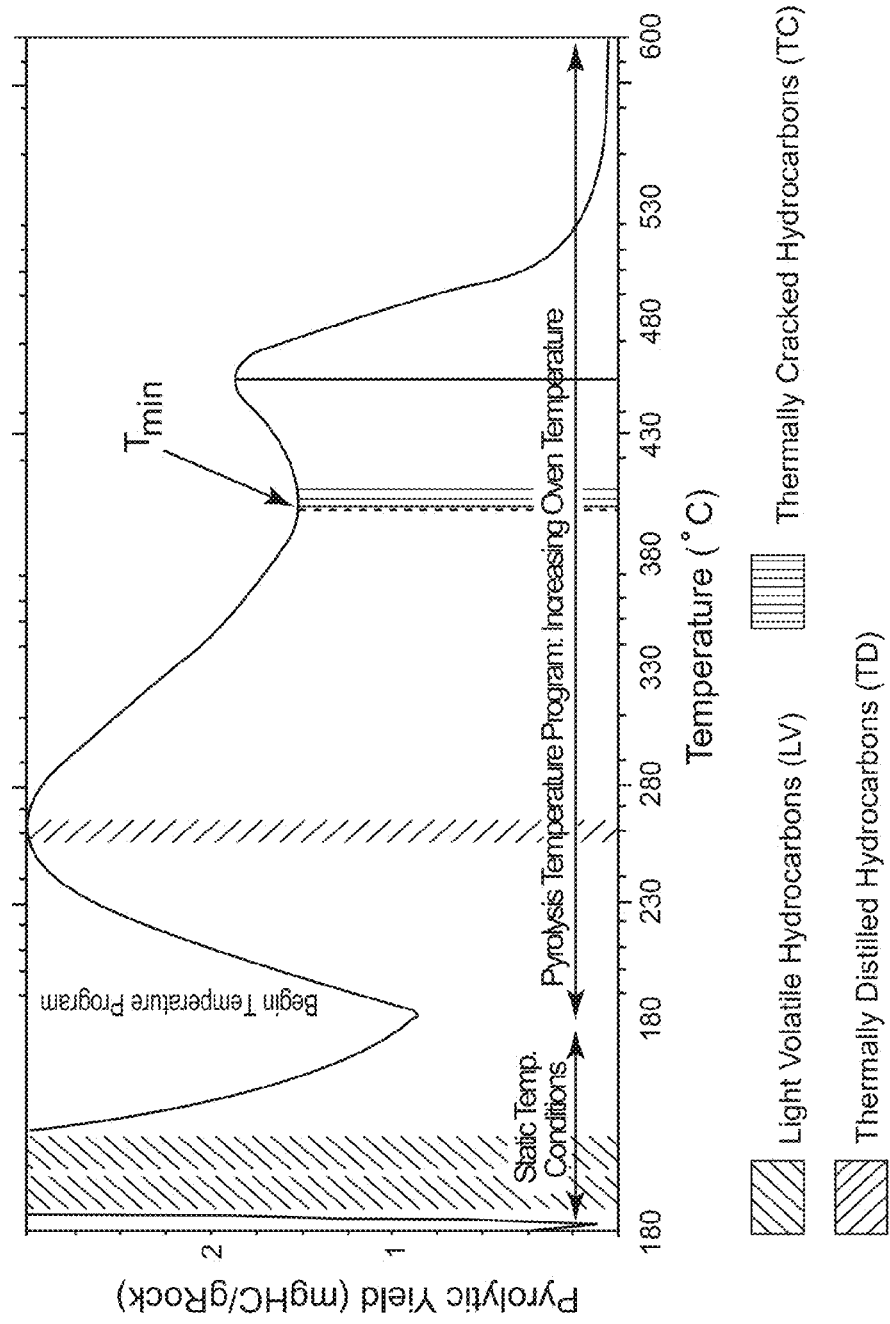
Figure 2A:
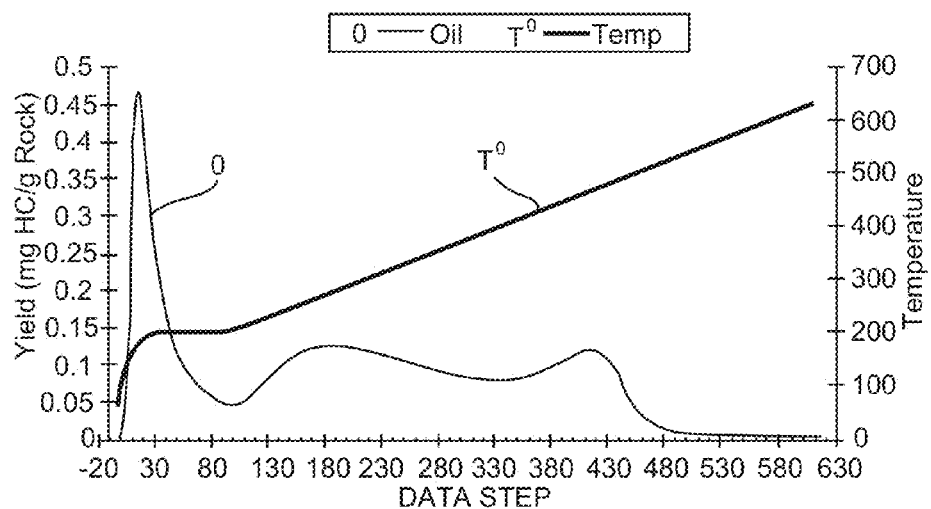
FIG. 2a is a typical pyrogram of API 30° oil from the K reservoir region.
Figure 2B:
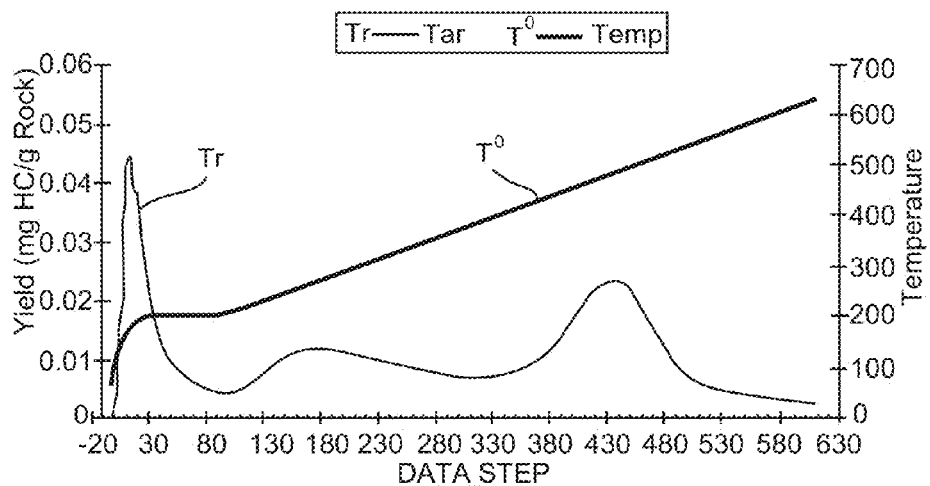
FIG. 2b is a typical pyrogram of tar from the K reservoir region.
Figure 2C:
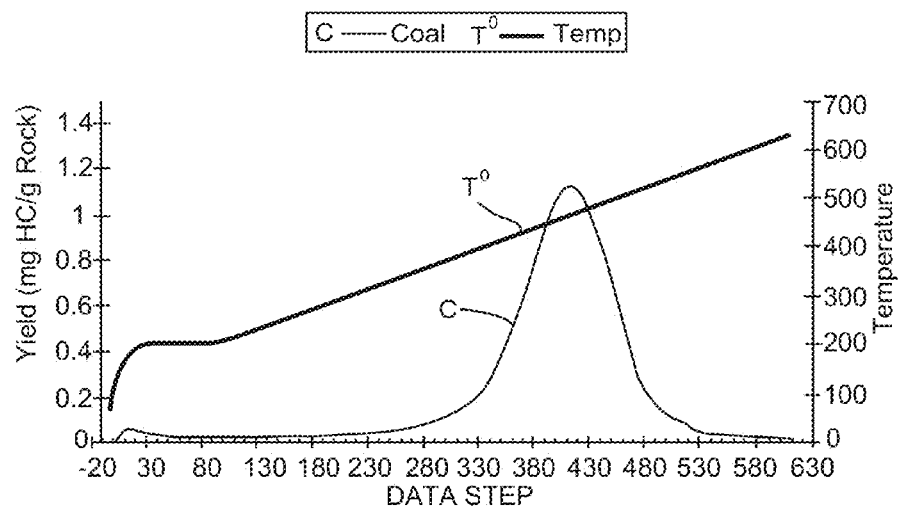
FIG. 2c is a typical pyrogram of coaly organic matter from the K reservoir region.
Figure 2D:
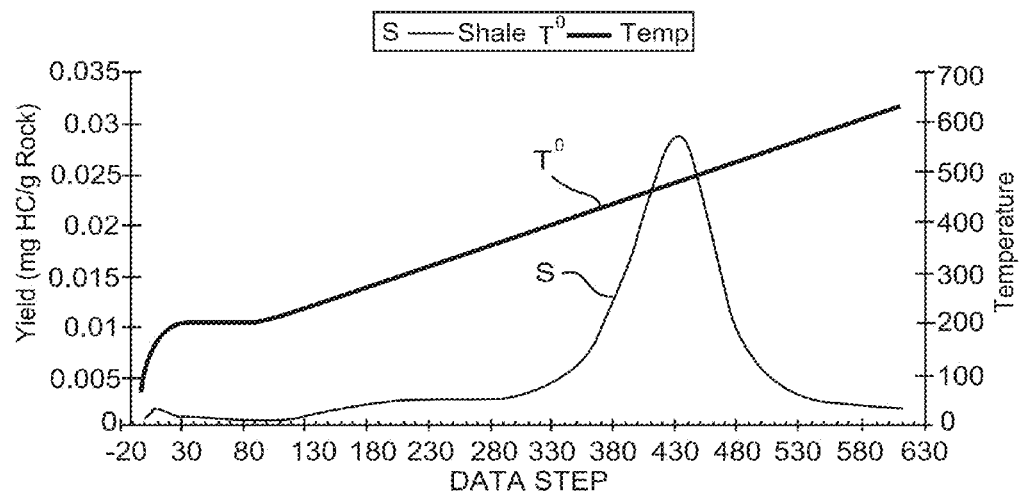
FIG. 2d is a typical pyrogram of organic-rich shale from the K reservoir region.
Figure 3:
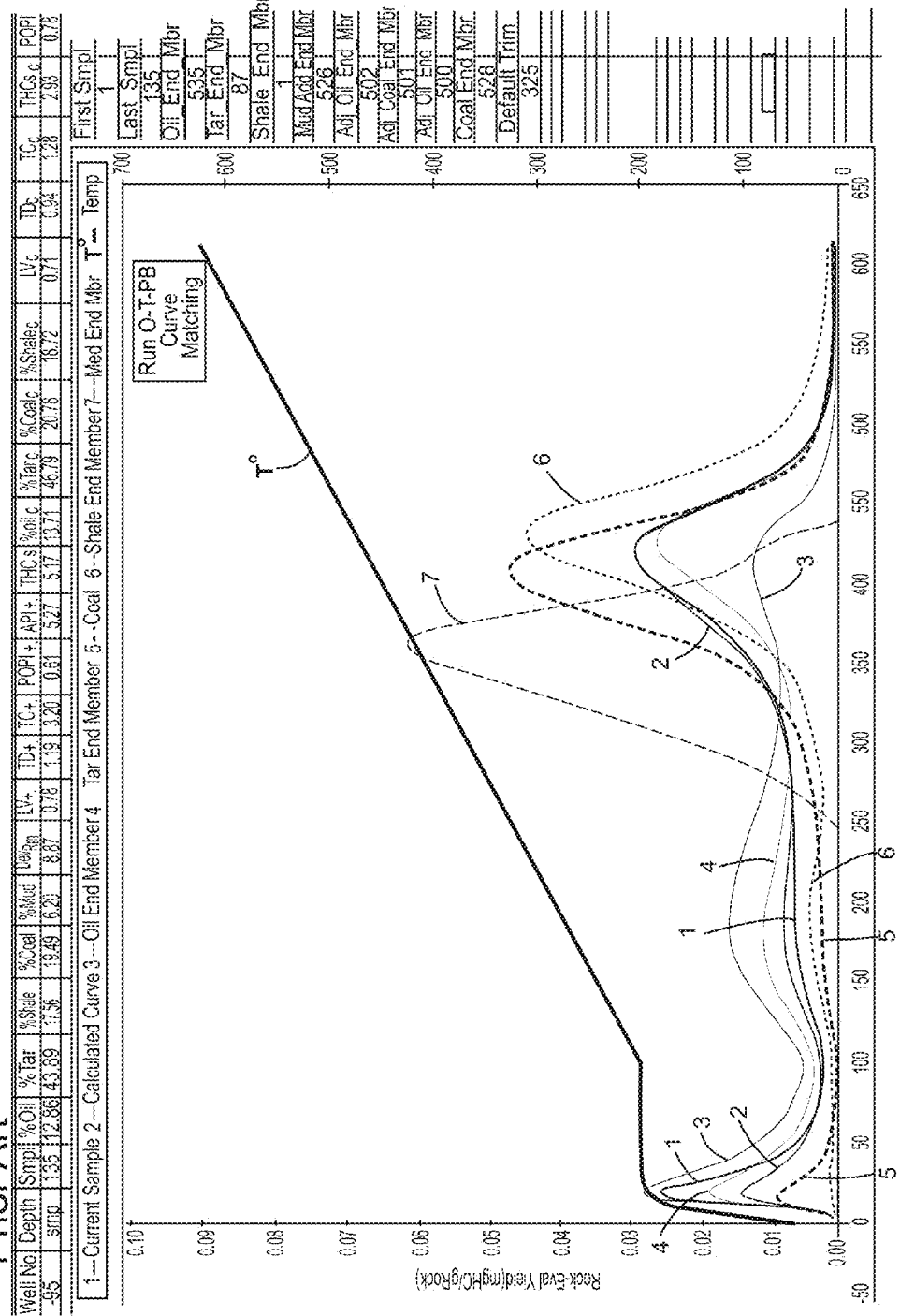
Figure 4:
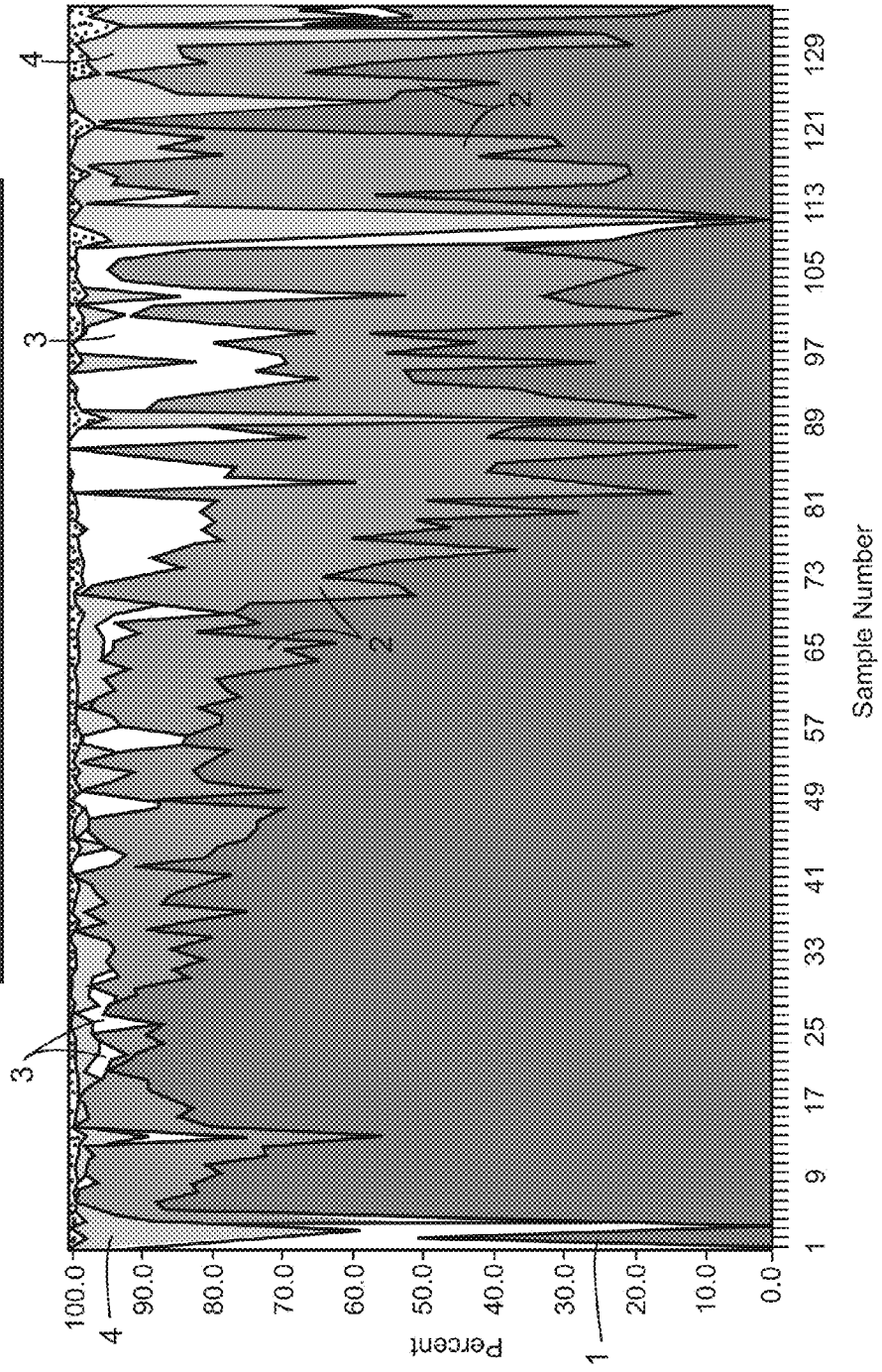
Figure 5:
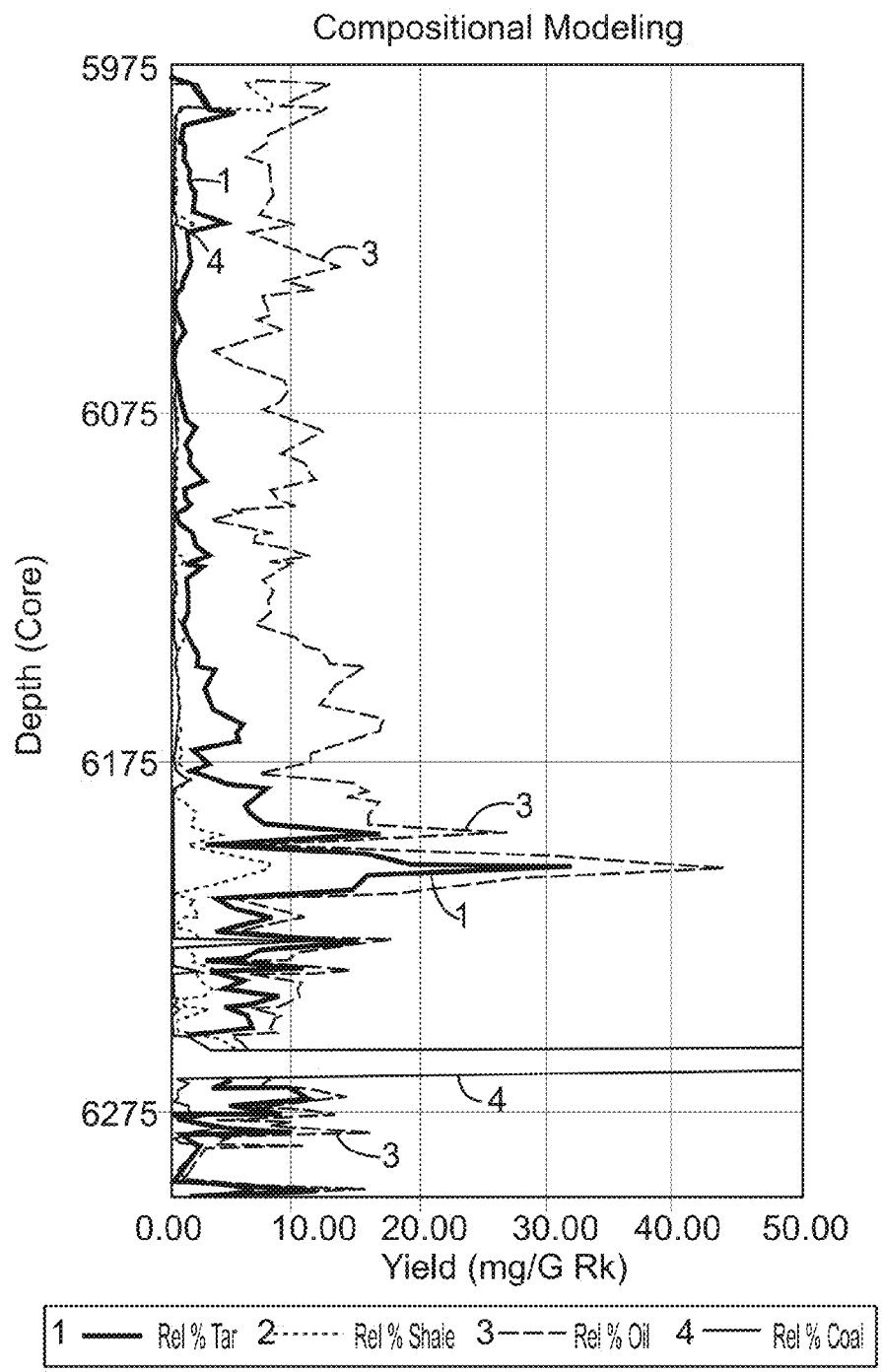

In applying the method for reconstructing the TOC from compositional modeling analysis, rock samples from a well are collected and analyzed in accordance with the methods described in U.S. Pat. Nos. 5,866,814, 6,823,298 and 7,363,206, the disclosures of which are incorporated herein by reference. In the use of the method of U.S. Pat. No. 7,363,206, it is necessary to identify the local end members that are suitable for use in applying compositional modeling. This is accomplished either by analyzing samples previously obtained from wells in the same field where the zone of interest is located as described below, or by relying exclusively on the samples collected from the well that is being assessed during exploratory or developmental drilling. Preferably, samples from other nearby similar wells are obtained. If there is no other analogue that is appropriate, then samples from the well being drilled could be used. However, this would provide less confidence in any interpretations made. If the samples are from the well being assessed, there can still be a need for real-time results.

Identifying appropriate end members can be accomplished by the examination of preexisting core samples, drill cuttings and electric logs that have been collected for the field or nearby wells. These sources will provide geologists and petroleum engineers with knowledge of the local oil fields and a basis for identifying the presence of organic-rich shales that are source rocks or unconventional reservoirs. Thus, typical steps in finding appropriate local organic end members would include collecting rock samples from zones where such organic matter occurrences have been noted in the equivalent geologic intervals from reservoir regions in proximity to the well that is being assessed.

Initial screening of data samples prepared and subjected to the pyrolytic oil-productivity index (POPI) method analysis as disclosed in U.S. Pat. No. 5,866,814 includes comparing resultant pyrograms to identify the similarity of curve shapes and serves to guide the user as to which samples are to be utilized for the organic matter separations and analysis steps that follow.

The basic pyrolysis analytical method as taught in U.S. Pat. No. 5,866,814 at column 3, line 51 to column 4, line 33, is preferred for use in the present invention. As used herein and specifically in the claims, the term "pyrolysis" shall mean the method disclosed in U.S. Pat. No. 5,866,814 and as described below. The disclosure of U.S. Pat. No. 5,866,814 is incorporated herein by reference.

In the pyrolytic analysis process, small samples (e.g., ≤100 mg) of powdered rock are placed in a steel crucible. The crucible is placed in a furnace and the sample is heated in a stream of helium gas to an initial temperature of 180 degrees C. After heating at 180 degrees C. for about three minutes, the temperature is increased. The rate of increase in the temperature is about 25 degrees C./min. or less, and preferably about 10 degrees C./min, and progresses from 180 degrees C. to about 600 degrees C.

The helium gas carries hydrocarbon products released from the rock sample in the furnace to a detector which is sensitive to organic compounds. During the process, the following three types of events occur:

1. Hydrocarbons that can be volatilized at or below 180.degree. C. are desorbed and detected while the temperature is held constant during the first 3 minutes of the procedure. These are called light volatile hydrocarbons (LVHC or LV).
2. At temperatures between 180 degrees C. and about 400 degrees C., thermal desorption of solvent-extractable bitumen, or the light oil fraction, occurs. These are called thermally distilled hydrocarbons or "distillables" (TDHC or TD).
3. At temperatures above about 400 degrees C., pyrolysis (cracking) of heavier hydrocarbons, or asphaltenes, occurs. The materials that thermally crack are called thermally cracked hydrocarbons or "pyrolyzables" (TCHC or TC).

These events give rise to three 'peaks' on the initial instrument output (referred to as a pyrogram). The peak for the static 180 degrees C. temperature is a standard output parameter of either the Vinci or Humble instruments. It is referred to as either $S_1$ or volatile total petroleum hydrocarbons (VTPH), respectively. In the present invention, the value will be referred to as light volatiles, LV, as described above. Data generated from the temperature-programmed pyrolysis portion of the procedure is reprocessed manually by the operator to determine the quantity of hydrocarbons in milligrams per gram of sample above and below $T_{min}$. This reprocessing is a trivial exercise for an experienced operator and can be accomplished routinely with either the Vinci or Humble instruments. The first peak above 180 degrees C. represents the amount of thermally distillable hydrocarbons in the sample and is referred to as TD, the second peak above 180 degrees represents the amount of pyrolyzables or thermally "cracked" hydrocarbons in the sample and is referred to as TC. In the case of lighter hydrocarbons or the analysis of oil samples directly for calibration, $T_{min}$ may not be discernable. In this case, if the sample analysis is repeatable at 400 degrees C., the values of LV, TD, and TC employed in the method of the present invention are with respect to the specific temperature ranges defined above.

The methods described in published application US 2010/0057409 are applied to identify the end members that are potentially present in the samples through screening and the analysis of consistent curve shapes. The samples are then subjected to physical separation of these components by solvent extractions to assess the uniformity of the organic matter in the samples. Cyclohexane is preferably used to separate any mobile, or "free" hydrocarbons present in the sample that could be produced from the well. Other saturated alkane solvents can also be used to provide similar results, but it has been found that cyclohexane produces an extract that often matches fluids actually produced from hydrocarbon-bearing zones.

After extraction of the component characteristic of mobile hydrocarbons, any remaining soluble organic matter is extracted. The soluble material found in the source rock or an unconventional reservoir will typically have a high asphaltene component and is representative of bitumen, which is formed early in the process of kerogen degradation during source rock maturation. A preferred solvent for bituminous compounds is dichloromethane, which is a strong organic solvent that can solubilize most asphaltenes and heavy hydrocarbon components. However, any other strong or highly polar organic solvent such as chloroform, carbon disulfide, and the like, can be used so long as it extracts all or most of the remaining soluble organic matter. The remaining insoluble organic matter in the sample after solvent extraction of the source rock can be representative of several materials, such as kerogen, inert carbon and recycled and oxidized organic matter.

After appropriate end members have been identified, the methods described in published application no. WO 2008/100614 (PCT/US2008/002102) are applied to determine the values for the Total Hydrogen Index (THI$_{OM}$), the ratio of organic matter-to-pyrolizable hydrocarbons (OM/HC$_{py}$), the ratio of hydrogen-to-carbon in the organic matter (H/C$_{OM}$), the percent of nitrogen, oxygen, and sulfur in the organic matter (NOS$_x$%), and the weight of hydrogen in the organic matter (Wt % H$_{OM}$).

These steps as taught in US 2010/0057409 at paragraphs [0062] to [0075], is preferred for use in the present invention and as described below. The disclosure of US 2010/0057409 is incorporated herein by reference.

In the assessment of reservoir rock samples, the goal is to characterize all of the hydrocarbons, whether they are "free" hydrocarbons or those bound in a complex structure. In addition, the methods differ in that the analytical procedure utilizes a starting temperature that is much lower (180° to 195° C.). Nonetheless, for each end-member, e.g., oil, tar and pyrobitumen, the amount of hydrocarbon by pyrolysis per gram of carbon will be fairly consistent. This parameter is referred to as the Total Hydrocarbon Index (THI) and is calculated as follows:

$$THI=[(LV+TD+TC)/TOC]\times 100 \qquad (6)$$

The units for THI are the same as HI, i.e., mg of hydrocarbon per gram of organic carbon. The Rock-Eval 6 or Humble POPI/TOC analyzers can be used to assess the differences in hydrogen for various end-members. THI is a ratio, with both TOC and THC (LV+TD+TC) determined during the same analysis, thus the errors associated with isolation of the OM, weighing, and small sample sizes that can occur in elemental analysis do not affect the data. It is important that sufficient separations of the organic end-members be obtained, so that results are consistent. Additional information that is needed for each organic matter end-member are the results from elemental analysis, i.e., as would be obtained from a CHNOS analyzer. With the percentage amounts of these elements and THI, the average amount of hydrogen present in the pyrolyzable and non-pyrolyzable portions of end-members can be determined in order to calculate the weight of the overall material. As stated above, the presence of heteroatoms in the various end-members and incomplete pyrolysis does result in some under-reporting of the quantity of hydrocarbon structural units based on the FID response. However, these effects are treated as contributing to the same result when assessing the pyrolyzable versus non-pyrolyzable portion of organic matter.

A typical separation of organic material in reservoir rock can be accomplished through a series of extraction/analytical steps. It is desirable to analyze the produced oil, which can be measured by placing a few microliters of oil on silica gel in a crucible and drying it in an oven at 30° C. for about 6 hours to remove the volatile components. The results of this analysis, plus CHNOS on the oil, provide a means for calculating the mass of oil per gram of rock contained in a sample. Another way of assessing the oil fraction is to extract the rock sample with cyclohexane. The extract that is obtained from this procedure will typically resemble the moveable hydrocarbons in the reservoir and the subsequent measurement of THI and CHNOS will provide data that are suitable for VOM analysis. In addition to the measurement of parameters for the extract, the THI and CHNOS data are also measured on the rock extracted with cyclohexane. This data represents the "immovable" bitumen remaining on the rock after cyclohexane extraction.

The next step in the process is to perform a second extraction on the cyclohexane extracted rock using a strong polar solvent, such as methylene chloride. The resulting extract is considered typical of the remaining tar or asphaltene component of the hydrocarbon staining, while the residual organic matter left in the rock consists of either pyrobitumen (tar that has been altered, lost a significant portion of its hydrogen, and become insoluble even in strong organic solvents) or another insoluble material like coal or kerogen. A variety of mechanisms have been proposed for the formation of pyrobitumen, including thermochemical sulfate reduction (TSR) and thermal alteration. However, there is no single accepted pathway. Nonetheless, hydrogen content in pyrobitumen is lower and the yield of hydrocarbon per gram of carbon is also lower. As with the cyclohexane extract and remaining rock, the methylene chloride extract and methylene chloride extracted rock are both analyzed by pyrolysis to determine the THI, and by elemental analysis for the CHNOS composition of the samples.

Determining Pyrolytic Yield and Mass/Volume Relationship for End-Members

The use of pyrolysis data to determine the volume of various organic constituents in the residual hydrocarbon staining is based on the determination of the Total Hydrocarbon Index for various reservoir organic matter (OM) types and the results from the previously described compositional modeling (CoMod) method. Detailed analysis of the end-members present in a reservoir is only needed for a limited number of samples in order to develop a relationship between the weight of the hydrocarbon component and the total weight of an end-member. Table 1 illustrates in tabular form the calculation steps required to develop the conversion factors for oil, tar and pyrobitumen and their application to determine the volume of end-members in conjunction with CoMod results. Since THI is based on the mg of hydrocarbon per gram of TOC, the composition of the end-members is also given relative to one gram of TOC. In addition, since pyrolysis instruments assess the weight of hydrocarbon in terms of mg per gram of rock, the amount of rock matrix assumed in this calculation is also 1 gram.

In this example, the results from Rock Eval 6 for this reservoir provide a THI of 1050, 525, and 250 respectively for the oil, tar, and pyrobitumen end-members. The results from elemental CHNOS analysis indicate that the end-members have H/C$_{OM}$ ratios of 1.9, 1.05, and 0.65, respectively, for oil, tar and pyrobitumen. Because the calculations are based on 1 gram of carbon, the weight of hydrogen in the organic matter based on elemental analysis in the sample can be calculated as follows:

$$\text{Wt. H}_{OM} \text{ (mg/1 g TOC)}=\text{H/C}_{OM}\times(1000 \text{ mg C/Mol} \cdot \text{Wt.}_{Carbon}) \qquad (7)$$

As stated previously, utilization of the combined pyrolysis and FID method results in the under-reporting of the weight-percent of hydrogen, because some of the hydrogen is associated with the pyrolyzable OM and some is associated with the non-pyrolyzable OM. Because the aliphatic bonds in complex molecules like asphaltenes and kerogen are most readily broken, it is assumed that the stoichiometry of aliphatic structural units, i.e., $-C_nH_{2n}$, are dominant in the pyrolyzable portion of the organic matter. This results in an average weight-percent for hydrogen in the pyrolyzable hydrocarbons (% H $C_nH_{2n}$) of 14.3%. Applying this assumption, the weight of hydrogen in the pyrolyzable hydrocarbons is determined as follows:

$$\text{Wt. } H_{HCP_y} \text{ (mg/1 g TOC)} = \%H\ C_nH_{2n}/100 \times THI(\text{mg HC/g TOC}) \times 1 \text{ g TOC} \quad (8)$$

The weight of hydrogen in non-pyrolyzable OM is determined as follows:

$$\text{Wt. } H_{Non-P_y}(\text{mg/1 g TOC}) = \text{Wt. } H_{OM}(\text{mg/1 g TOC}) - \text{Wt. } H_{HCP_y}(\text{mg/1 g TOC}) \quad (9)$$

In accordance with the method of the present invention, the weights of hydrogen in the non-pyrolyzable portion of oil, tar and pyrobitumen for this example are 8.2 (mg/1 g TOC), 12.4 (mg/1 g TOC), and 18.4 (mg/1 g TOC), respectively. Thus, the assumption that the hydrocarbon liberated from organic matter by pyrolysis is dominated by aliphatic units result in an under-reporting of hydrogen that is relatively large for tar (14.2%) and even larger for pyrobitumen (34%). Moreover, assuming that the average composition of the measured hydrocarbons from pyrolysis-FID has a lower H/C ratio, would only increase the hydrogen under-reporting from pyrolysis, which would necessitate a larger correction.

In order to simplify the approach, in the method of the invention the $-C_nH_{2n}-$ structural units are assumed to be the dominant form that is produced by pyrolysis of organic matter from petroleum reservoirs. However, it should be noted that the error involved in misrepresenting the amount of hydrogen in the sample is relatively small. For example, the 18.4 mg H/1 g TOC under-reporting for hydrogen in pyrobitumen would result in only a 1.75% error if totally disregarded. When the purpose of the calculations is to assess the volume of tar in a reservoir, and the critical amount of tar present is around 5% of the volume, it will be understood that the difference between 4.9% and 5.1% tar by volume is not significant.

Once the respective weights for hydrogen in the sample have been determined, the weight of carbon in the pyrolyzable OM and non-pyrolyzable OM can be calculated as follows:

$$\text{Wt. } C_{HCP_y} \text{ (mg/1 g TOC)} = THI \text{ (mg/1 g TOC)} \times 1 \text{ g TOC} - \text{Wt.} H_{HCP_y} \text{ (mg/1 g TOC)} \quad (10)$$

$$\text{Wt. } C_{Non-P_y}(\text{mg/1 g TOC}) = 1000 \text{ mg TOC} - \text{Wt. } C_{HCP_y} \text{ (mg/1 g TOC)} \quad (11)$$

The elemental composition analysis of crude oils shows that elemental NSO typically comprise between 1-4% and asphaltene fractions will typically range from 5-12%. In the present example, the NSO values determined for the oil, tar and pyrobitumen were 2.8%, 7.3%, and 7.6%, respectively, which is within the range noted in the literature. For example, see Ancheyta, et al., Energy and Fuels, Vol. 16, pp 1121-27, 2002; Holleran, VSS Technology Library, Valley Slurry Seal Company, www.slurry.com/techpapers contrbit.shtml, 2000. Thus, from CHNOS elemental analysis, the weight-percent attributed to elemental nitrogen, sulfur and oxygen in the sample can be readily determined. Once these values have been determined, the weight of this material in the organic end-member can be calculated as follows:

$$\text{Wt.} NSO_{OM} = \frac{(\%NSO_{OM}/100) \times \left(\text{Wt.} C_{HCP_y} + \text{Wt. } C_{Non-P_y} + \text{Wt. } H_{HCP_y} + \text{Wt.} H_{Non-P_y}\right)}{(1 - (\%NSO_{OM}/100))} \quad (12)$$

The total weight of organic matter for each end-member can be calculated relative to 1 gram of TOC and the ratio of organic matter to pyrolyzable hydrocarbon (OM/HC$_{P_y}$) can be determined as follows:

$$\text{Wt. OM (mg/1 g TOC)} = \text{Wt. } H_{HCP_y} + \text{Wt. } H_{Non-P_y} + \text{Wt. } C_{HCP_y} + \text{Wt. } C_{Non-P_y} + \text{Wt.NSO}_{OM} \quad (13)$$

$$OM/HC_{P_y} = \text{Wt. OM/THI, or} \quad (14)$$

$$OM/HC_{P_y} = \text{Wt. OM}/(\text{Wt. } H_{HCP_y} + \text{Wt. } C_{HCP_y}) \quad (15)$$

As with the weight of hydrogen in the sample, variations in the amount of elemental NSO in organic matter within a reservoir are not likely to affect the estimated volume of organic matter by more than a few percent. It is important to determine suitable end-members that produce accurate CoMod results. Since OM/HC$_{P_y}$ ratios for the example shown were 1.13 for oil, 2.23 for tar, and 4.56 for pyrobitumen, errors in the modeling process are far more important than minor errors associated with the chemical make-up of these materials. Therefore, it is particularly important to confirm modeled results with laboratory separations that show that the relative amount of soluble versus insoluble materials is similar. This is because a 5% volume of pyrobitumen has a response that is equal to about 2.5% volume of tar.

Finally, the quantity of inert carbon (TOC$_{inert}$) in the samples is determined by plotting TOC versus hydrocarbon yield in accordance with well known and commonly applied methods, such as those described by Langford, F. F. and M.-M. Blank-Valleron, 1990, Interpreting Rock-Eval Pyrolysis Data Using Graphs of Pyrolizable Hydrocarbons vs. Total Organic Carbon, Bulletin of the American Association of Petroleum Geologists, v. 74, p. 799-804; Dahl, B., J. Bojesen-Koefoed, A. Holm, H. Justwan, E. Rasmussen, and E. Thomsen, 2004, A New Approach to Interpreting Rock-Eval S2 and TOC Data for Kerogen Quality Assessment, Organic Geochemistry, v. 35, pp. 1461-1477, and others.

With these parameters and other data entered in the memory of the appropriately programmed general purpose computer, the results from applying compositional modeling as described in U.S. Pat. No. 7,363,206 for each end member (EM) are used to calculate the hydrocarbon yield that is attributable to each end member (Yield$_{EMx}$) in a group of samples from a source rock or unconventional reservoir. From this data, the weight of organic matter represented by each sample's hydrocarbon yield can be calculated by utilizing the ratio of the organic matter to pyrolizable hydrocarbons (OM/HC$_{pyx}$) as follows:

$$EM_x \text{ Weight OM} = Yield_{EMx} * OM/HC_{pyx} \quad (16)$$

The weight of elemental nitrogen, sulfur, and oxygen is calculated as follows:

$$EM_x \text{ Weight NSOs} = NOS_x\% * EM_x \text{ Weight OM} \quad (17)$$

Next, the weight of Hydrogen is calculated as follows:

$$EM_x \text{ Weight H} = \text{Wt \%} H_{OM} * EM_x \text{ Weight OM} \quad (18)$$

Finally, the weight of total organic carbon for the end member ($TOC_{EMx}$) is calculated as follows:

$$TOC_{EMx} \text{ (wt. \%)} = (EM_x \text{ Weight OM (mg/g Rock)} - EM_x \text{ Weight NSOs (mg/g Rock)} - EM_x \text{ Weight H (mg/g Rock)}) \times 100/1000 \text{ mg/g Rock} \quad (19)$$

After the TOC for each end member component is calculated, they are summed and the inert carbon present in the formation as determined from a nearby well using standard methods is added to yield the reconstructed total organic carbon ($TOC_{RCN}$ or $TOC_{CoMod}$) as follows:

$$TOC_{RCN} = TOC_{EM1} + TOC_{EM2} \ldots TOC_{EMx} + TOC_{inert} \quad (20)$$

Figure 7:
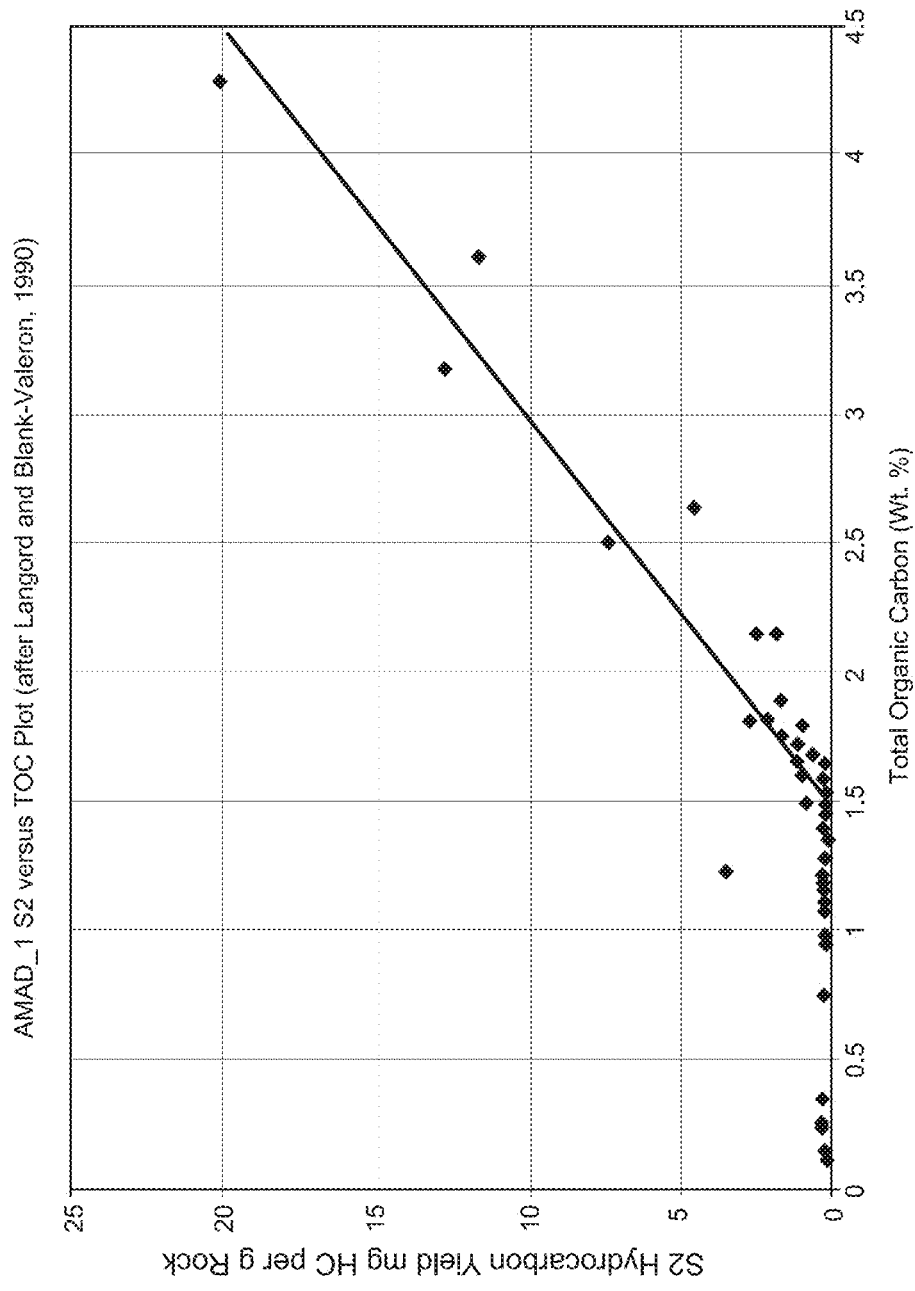
FIG. 7 is a plot of S2 hydrocarbon yield versus TOC for the nearby "AMAD-1" well.

The method for determining of the quantity of "inert carbon" in a rock sample is well established in the art of source rock analysis, and is described, for example, in Langford, F. F. and M.-M. Blank-Valleron, 1990, Interpreting Rock-Eval Pyrolysis Data Using Graphs of Pyrolizable Hydrocarbons vs. Total Organic Carbon. For the example from AMAD_2, reference is made to FIG. 7 where there is shown a plot of S2 Hydrocarbon Yield versus TOC for a nearby well, AMAD_1, which is used to assess the amount of inert carbon by noting the X-intercept of the resultant trend line.

Example 1

The following example of the method of the present invention uses the compositional modeling analysis method based on POPI data to calculate reconstructed total organic carbon (TOC) values. It has been found that reconstructed TOC values closely correspond to TOC measurements by standard instruments. The method of the invention can be used in unconventional oil reservoirs to provide relevant data in real time at the well site for use in making operational decisions while drilling. In addition to providing TOC data, the method also provides data that discriminates among the organic matter found the reservoir rock, such as free oil, residual bitumen and kerogen.

The data for this example is based upon data derived from core samples collected from an Arabian well identified as DBYT-1 that were analyzed for TOC and also by standard POPI analysis. The POPI data were processed by the GC-ROX™ commercial software available from the Saudi Arabian Oil Company and the compositional modeling method in order to assess the relative contribution of each organic matter end member to the total pyrolytic signature.

Figure 8:
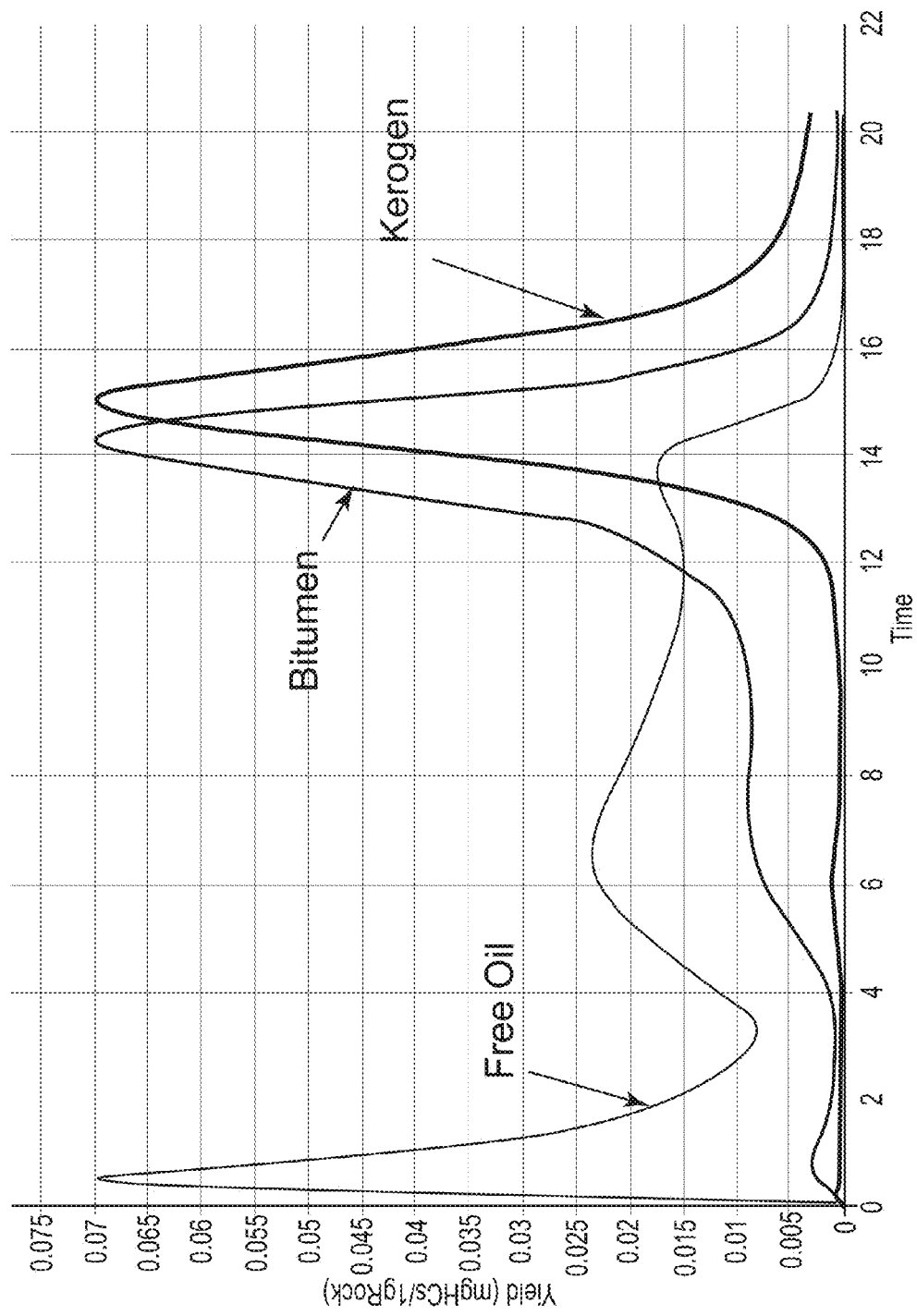
FIG. 8 is a plot of the end member pyrograms used for modeling a well identified as "DBYT-1"

Shown in FIG. 8 is a plot of the end member pyrograms used to model the DBYT-1 well. The curve labeled "Free Oil" is representative of the free oil in the reservoir and was obtained by a cyclohexane extraction of the rock samples collected during drilling. Notably, the API gravity values for these samples as assessed by ranged between 32° and 34°. API was determined by pyrolysis methods disclosed in U.S. Pat. No. 6,823,298 B1. The "Bitumen" curve is representative of residual bitumen present in the formation that was obtained by extraction of the rock samples using methylene chloride. Its appearance is typical of what is observed for asphaltene fractions. The "Kerogen" curve is characteristic of the kerogen found in the reservoir and was determined by pyrolytic analysis of the rock samples after the above extractions by cyclohexane and methylene chloride.

Figure 9:
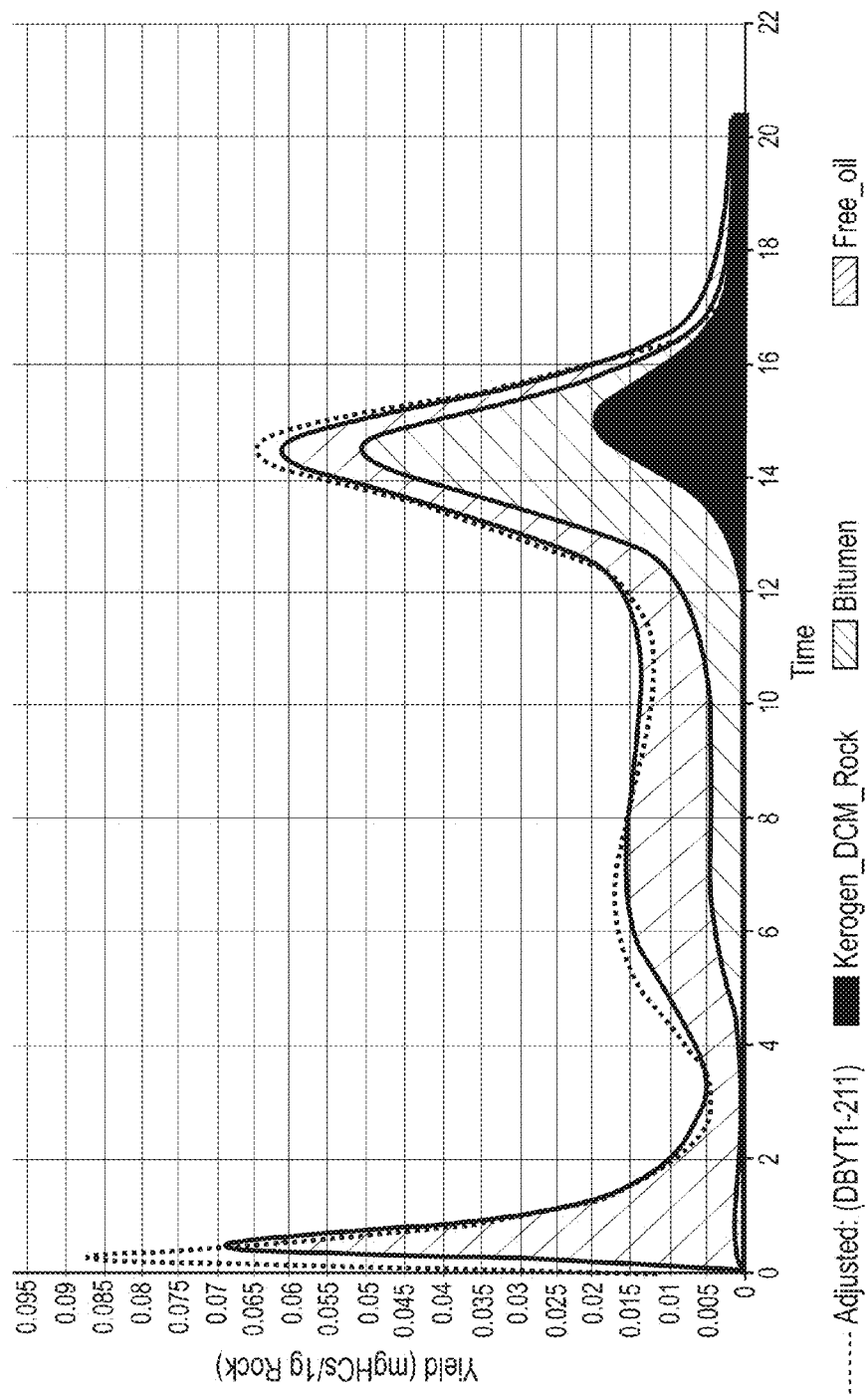
FIG. 9 shows the results from modeling a typical pyrogram from the same DBYT-1 well.

Referring to FIG. 9, there are shown the results from modeling a typical pyrogram from the DBYT-1 well. The "Adjusted: (DBYT1-211)" curve is the actual sample data and the pattern-filled curve shows the results from the application of compositional modeling as a summation of the relative components of the end members. Notably, the model solution under estimates the amount of light components present in the LV (light volatile) portion of the pyrogram. This lower value reflects losses typically encountered in the light ends from extraction processes and also suggests that significant light components are in fact present the reservoir rock. The modeling results show high levels of free oil throughout the entire interval sampled.

Figure 10:
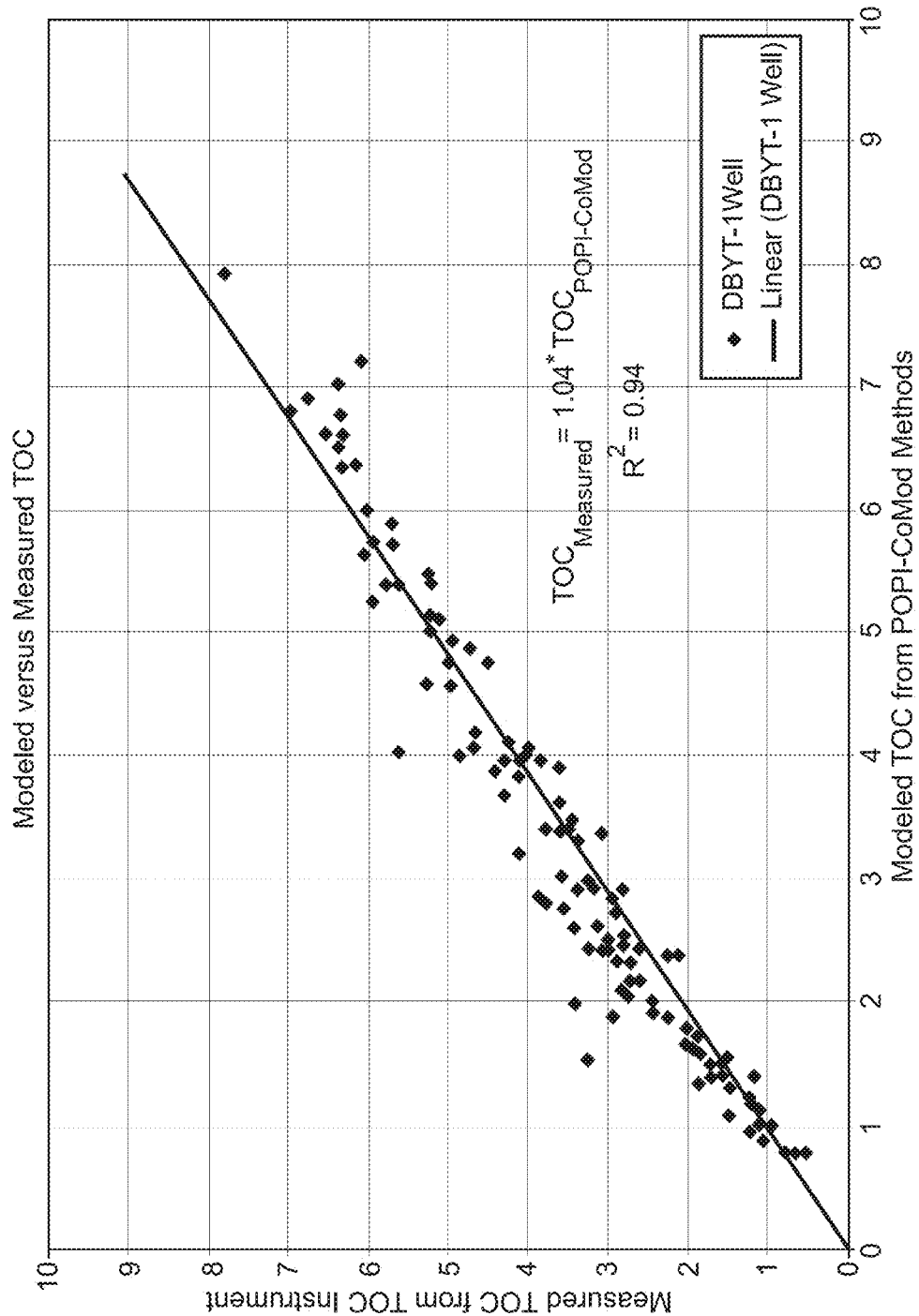
FIG. 10 is a plot comparing the determination of TOC from modeling POPI data to measured TOC from instrumental data.

Shown in FIG. 10 is a plot comparing the determination of TOC from modeling POPI data to measured TOC from instrumental data. The slope for the least squares fit of the line is very close to 1 with a high correlation coefficient. The results indicated a very robust correlation and provide confirmation of the utility and reliability of compositional modeling in determining the relative quantities of organic matter components in the source rocks.

In order to convert POPI data into TOC values, compositional modeling was used to determine the relative abundance of each end member in a rock sample. The chemical and physical properties of those end members were then used to calculate the weight percentage of both the pyrolyzable and non-pyrolyzable portions of each component. Significantly, the contribution of these three relatively simple components can be varied to achieve viable acceptable matches with actual rock samples. This implies that the model being used is a plausible representation of the organic matter distribution found in the rocks. The results can also form the basis to infer the level of transformation of organic matter into hydrocarbons that has occurred in the source rocks.

Figure 11:
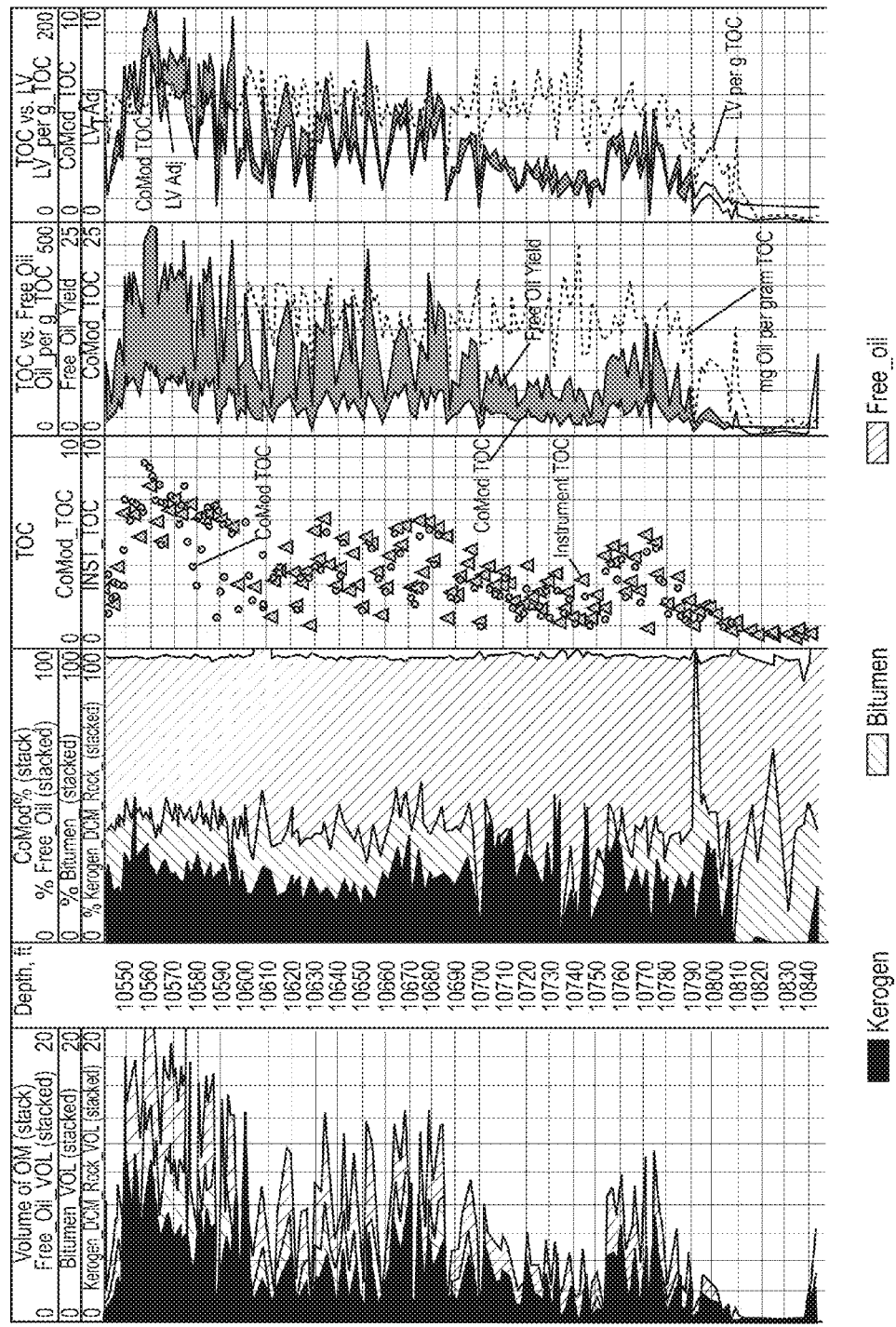
FIG. 11 is a composite log generated by the GC-ROX software for the DBYT-1 well.

Shown in FIG. 11 is a composite log of five tracks from the GC-ROX™ software for a 290 foot section of the DBYT-1 well. In track one, a stack presentation of the volume of organic matter data from each end member is shown. In track two, the stack presentation of the modeled percentages of the end members from compositional modeling (CoMod %) are plotted. In track three, the value of TOC calculated from compositional modeling is plotted (circles) along with instrument measurements of TOC (triangles) for a large selection of the samples. In track four, TOC is compared with the quantity of the free oil in rock samples expressed as mg oil per gram of rock sample. In track five, CoMod TOC and light volatiles (LV) hydrocarbon yield per gram of TOC are plotted to illustrate the crossover significance as described below relative to the reference by Jarvie effect. Note that the "LV adj." entry on plot is basically LV, but GC-ROX performs quality control during sample import and adjusts the yields slightly due to baselining procedures and smoothing algorithms.

Examination of the data presented in tracks one and two show a very high level of free oil throughout the DBYT-1 well. However, this data is difficult to compare with published accounts of unconventional oil reservoirs that use other parameters. This comparison is difficult because prior art methods rely on simple bulk integration and temperature cutoffs and do not distinguish the actual organic matter types present in the samples.

In track three, as shown in the cross plot of TOC data, there is a very close correspondence between the values of measured TOC and TOC calculated from CoMod. This plot justifies a high confidence level in the patterns that are shown in the plots from the pyrolysis data.

In tracks four and five, plots were constructed that are similar to published methods used for the assessment of unconventional oil reservoirs. From the standpoint of organic matter in hydrocarbon, the most commonly relied upon method of the prior art is to compare the TOC obtained by the Rock-Eval method and the S1 yield. As shown in Jarvie 2011, in press, AAPG Memoir 97, Shale reservoirs—Giant resources for the 21st century, J. Breyer, ed., in press, Jarvie, Daniel M., 2012, Shale resource systems for oil and gas: Part 1—Shale gas resource systems; Part 2—Shale oil resource systems, AAPG Memoir 97, p. 69-119, the preferred form of presenting the data is to plot S1 values and TOC values using the same scale. When S1 exceeds the value for TOC, these regions are said to exhibit crossover and are inferred to be favorable for unconventional oil production.

In the analysis shown in FIG. 11, two somewhat different plots are shown: one is TOC plotted against the yield of free oil and the other is TOC plotted against the LV (light volatile) yield. Neither one of these reflects precisely the determination of S1 yield. In the Rock-Eval method, S1 yield is determined by the hydrocarbons that are liberated at 300° C., whereas the LV yield is the amount of hydrocarbons liberated at 195° C. Thus, the LV yield is more conservative than S1 yield. The free oil yield as determined from compositional modeling represents the actual oil in any sample; however, it is possible that this results in a greater value than the simple S1 yield. However, the use of S1 yield at 300° C. is meant to represent the light hydrocarbons present in rock samples, and utilizing free oil values from compositional modeling is at present believed to be a viable indicator with good accuracy.

Both techniques of plotting light hydrocarbon yield versus TOC result in significant observed crossover effects in the DBYT-1 well. This suggests that the sampled section at the DBYT-1 well compares very favorably to productive unconventional oil reservoirs found as proven resources in North America.

Actual testing of the DBYT-1 well based on the method of the invention resulted in the recovery of some oil despite difficulties that occurred during well site operations and the testing procedures. In view of the fact that a great deal of the success in completing unconventional oil reservoirs in North America come only after significant investments in experimental well drilling and completion methods, the geochemical results from the DBYT-1 represent a viable method for future exploration and development drilling.

Example 2 and 3

The method described above was applied to samples from the DBYT-1 and AMAD-2 wells to yield the results set forth in Table 2 shown in FIGS. 12A-B and Table 3 shown in FIGS. 13A-B, respectively.

Figure 14:
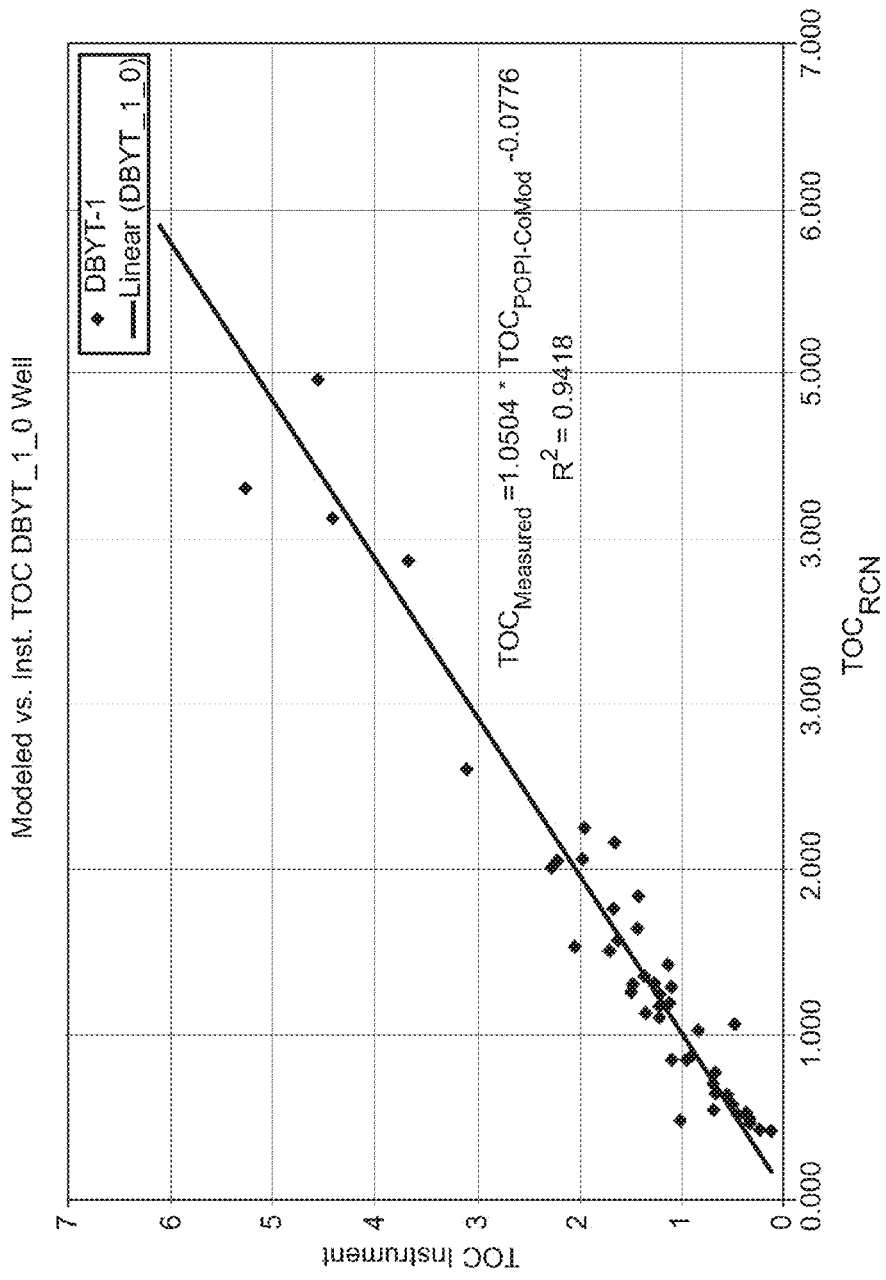
FIG. 14 is a cross-plot of instrument TOC versus reconstructed TOC ($TOC_{RCN}$) from the DBYT-1 well.
Figure 15:
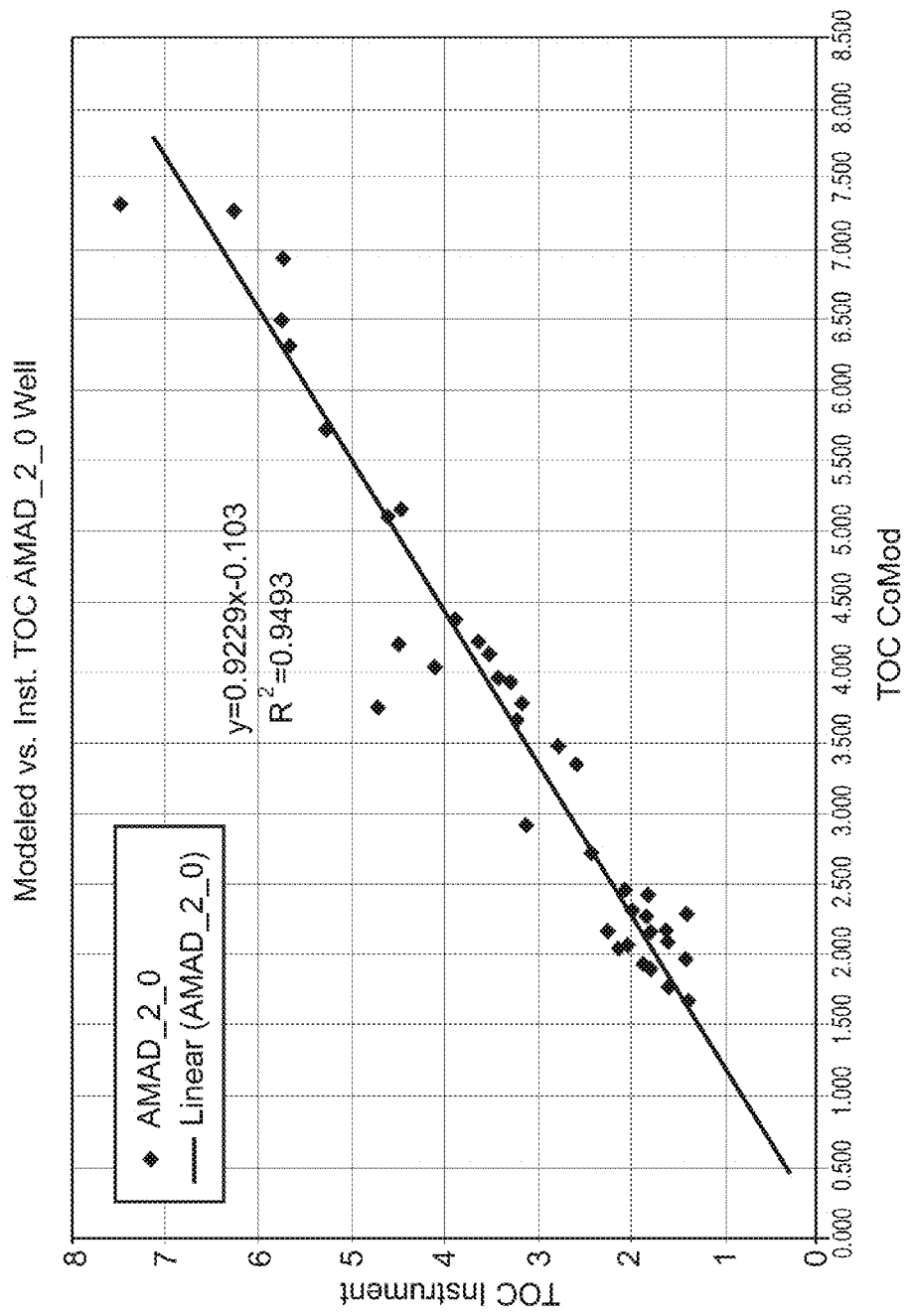
FIG. 15 is a cross-plot of instrument TOC versus reconstructed TOC ($TOC_{RCN}$) from a well identified as "AMAD-2"

FIG. 14 is a cross-plot of instrument measurements of the TOC versus reconstructed TOC ($TOC_{RCN}$) from the DBYT-1 well data reported in Table 2 and FIG. 6 is a cross plot of instrument measurements of the TOC versus reconstructed TOC ($TOC_{RCN}$) from the AMAD-2 Well data reported in Table 3. The plots of FIGS. 14 and 15 demonstrate that TOC calculations that are reconstructed from compositional modeling provide a very close correlation to TOC values that are based on instrument measurements. The least squares fit of the line for the respective plots were as follows: DBYT-1, the $R^2$=0.9418 and for AMAD-2 the $R^2$=0.9493.

Example 4

Figure 16:
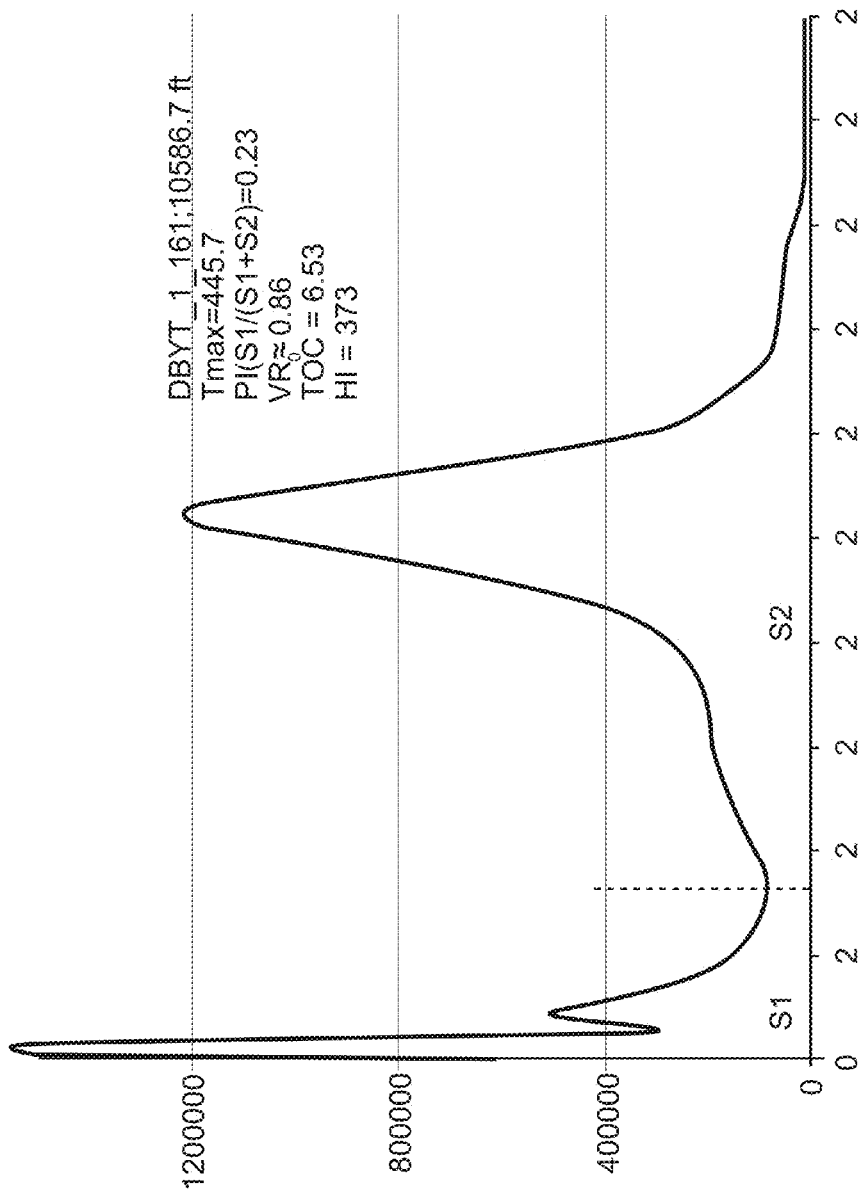
FIG. 16 is a plot of the pyrogram for a representative sample from well DBYT-1 produced during standard Rock-Eval analysis.

An example of the improved interpretations provided through the reconstructed TOC method is illustrated by comparison of data from the DBYT-1 well to another potential unconventional oil resource well (MZLJ-29). FIG. 16 is a plot of the pyrogram for a representative sample from DBYT-1 produced during standard Rock-Eval analysis; i.e., using a starting temperature of 300° C. to capture the S1 hydrocarbon yield (in mg hydrocarbons/g Rock) and then programmed pyrolysis at 25° C./minute to 600° C. to capture the S2 hydrocarbon yield. As mentioned previously, the S1 hydrocarbon yield is commonly taken as representative of the "Free Oil" content of a sample. For example, see Jarvie, Daniel M., 2012, Shale resource systems for oil and gas: Part 1—Shale gas resource systems; Part 2—Shale oil resource systems, AAPG Memoir 97, p. 69-119.

Figure 17:
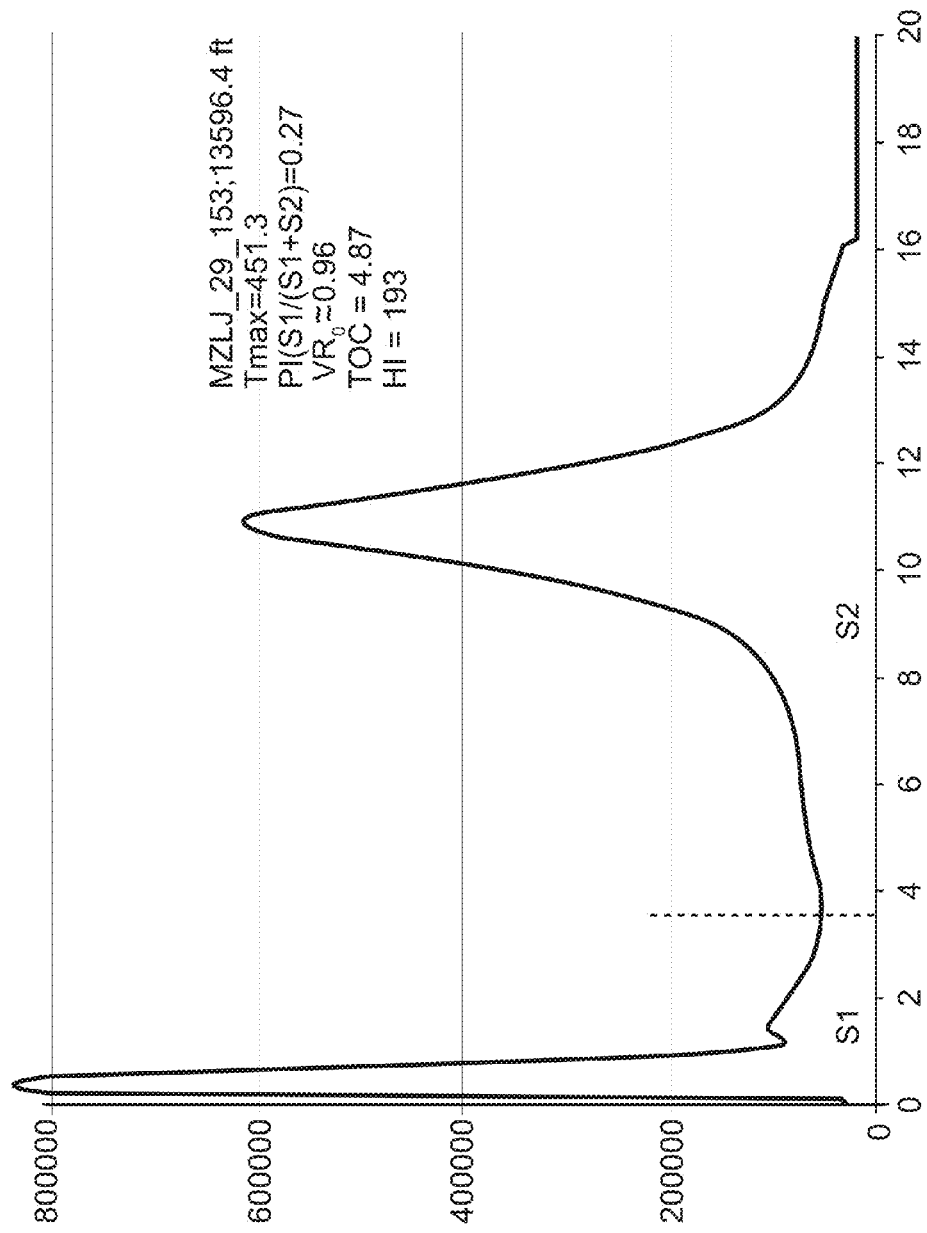
FIG. 17 is the corresponding plot for a representative sample from well MZLJ-29.

FIG. 17 is the corresponding plot for a representative sample from MZLJ-29. The corresponding parameters commonly used for source rock/unconventional reservoir analysis are annotated on the plot. For both of these wells, the relative abundance of the "Free Oil" component as represented by S1 hydrocarbon yield is similar, with the Production Index (PI: S1/(S1+S2)) equal to 0.23 for DBYT-1 and 0.27 for MZLJ-29. This data would suggest a somewhat greater "Free Oil" content for MZLJ-29 than DBYT-1; however, the difference is not significant. Other parameters, such as the value of Tmax (445.7 for DBYT-1 vs. 451.3 for MZLJ-29) and the Hydrogen Index (HI; 373 for DBYT-1 vs. 193 for MZLJ-29) also suggest that greater organic matter transformation has occurred at the MZLJ-29 well.

Figure 18:
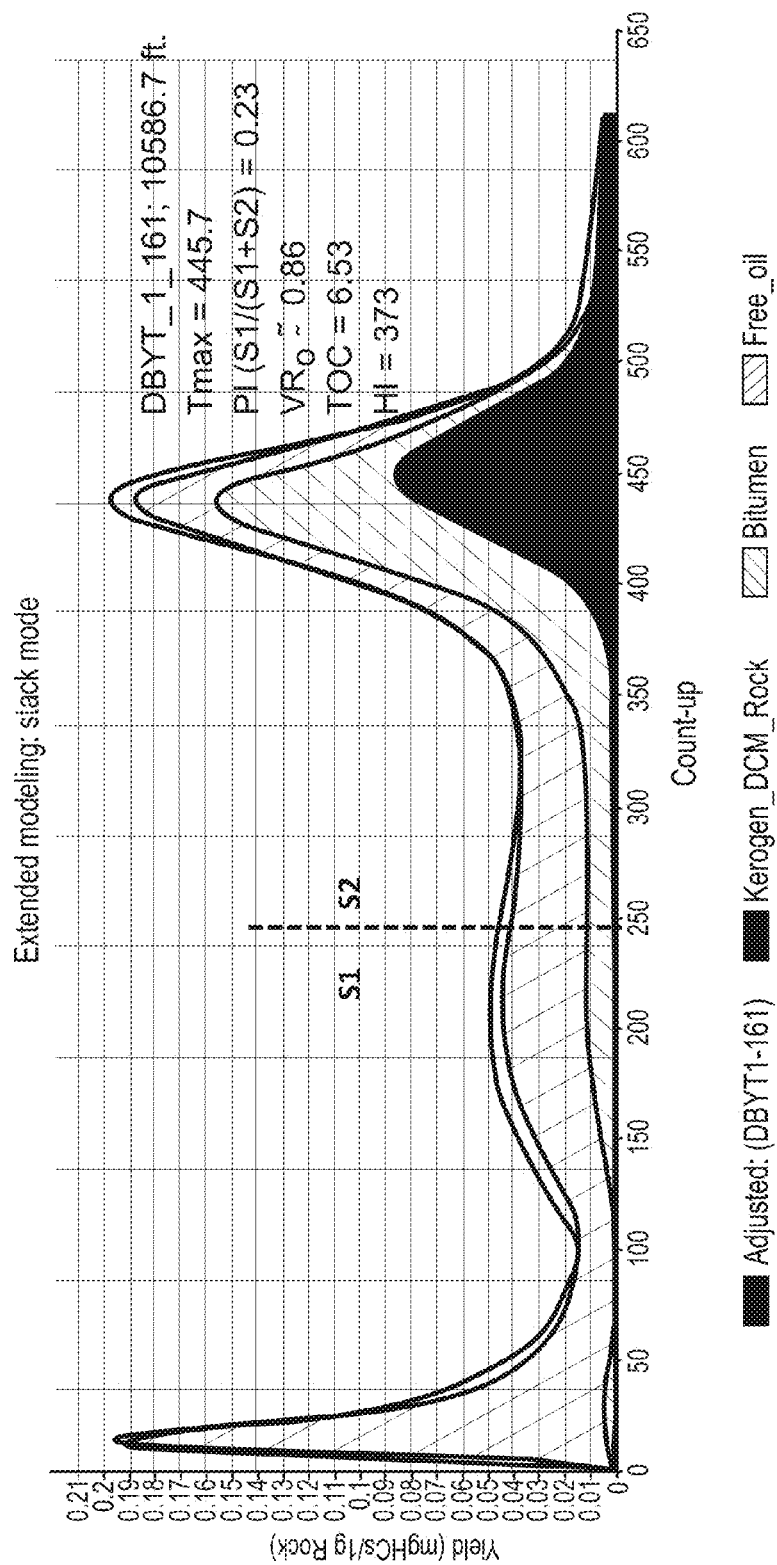
FIGS. 18 and 19 are the corresponding plots of the samples of FIGS. 14 and 15 when assessed by the method of the invention.
Figure 19:
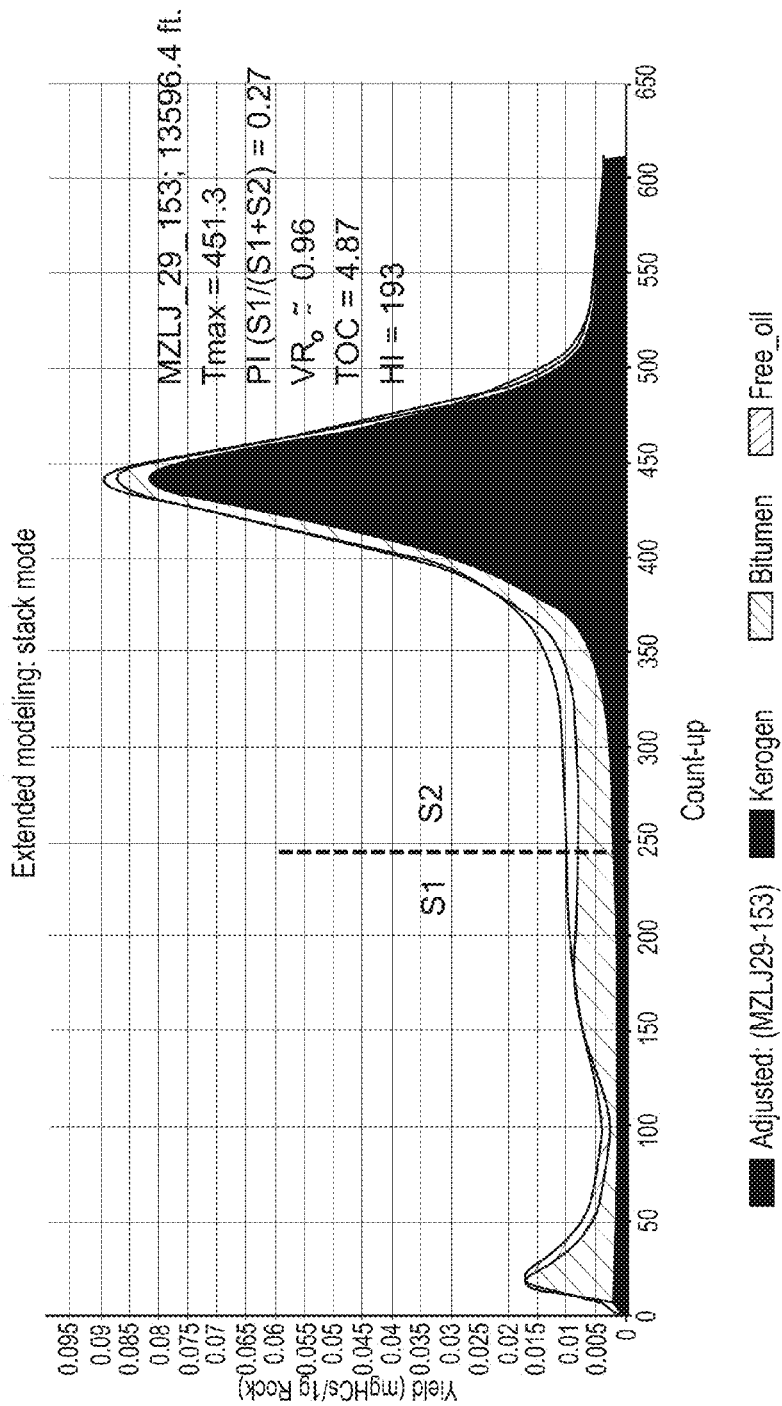

FIGS. 18 and 19 are the corresponding plots of the same samples as assessed by the method of the invention. These samples were run with the standard analytical procedure as provided in the POPI method (U.S. Pat. No. 5,866,814) and subsequent application of the Compositional Modeling method (U.S. Pat. No. 7,363,206). In these plots, the original data are shown by the black solid pyrogram line and the results of Compositional Modeling are shown by the pattern-filled pyrogram, where the amount of each end-member for "Free Oil," "Bitumen," and "Kerogen" are reflected by the respective patterns in the legend. In this case, it can be clearly seen that the sample from the DBYT-1 well shows abundant "Free Oil," whereas, the sample from the MZLJ-29 well shows almost no "Free Oil." Also annotated on these plots, is the approximate division between material that would normally be comprised of S1 and S2 hydrocarbon yields under the standard Rock-Eval analysis. As can be clearly observed, a large amount of "Bitumen" can be associated with the early portion of a pyrolysis run. Significant differences are observed in the curve shape by using a lower starting temperature, which allows the differentiation between "Free Oil" and "Bitumen" end members.

Figure 20:
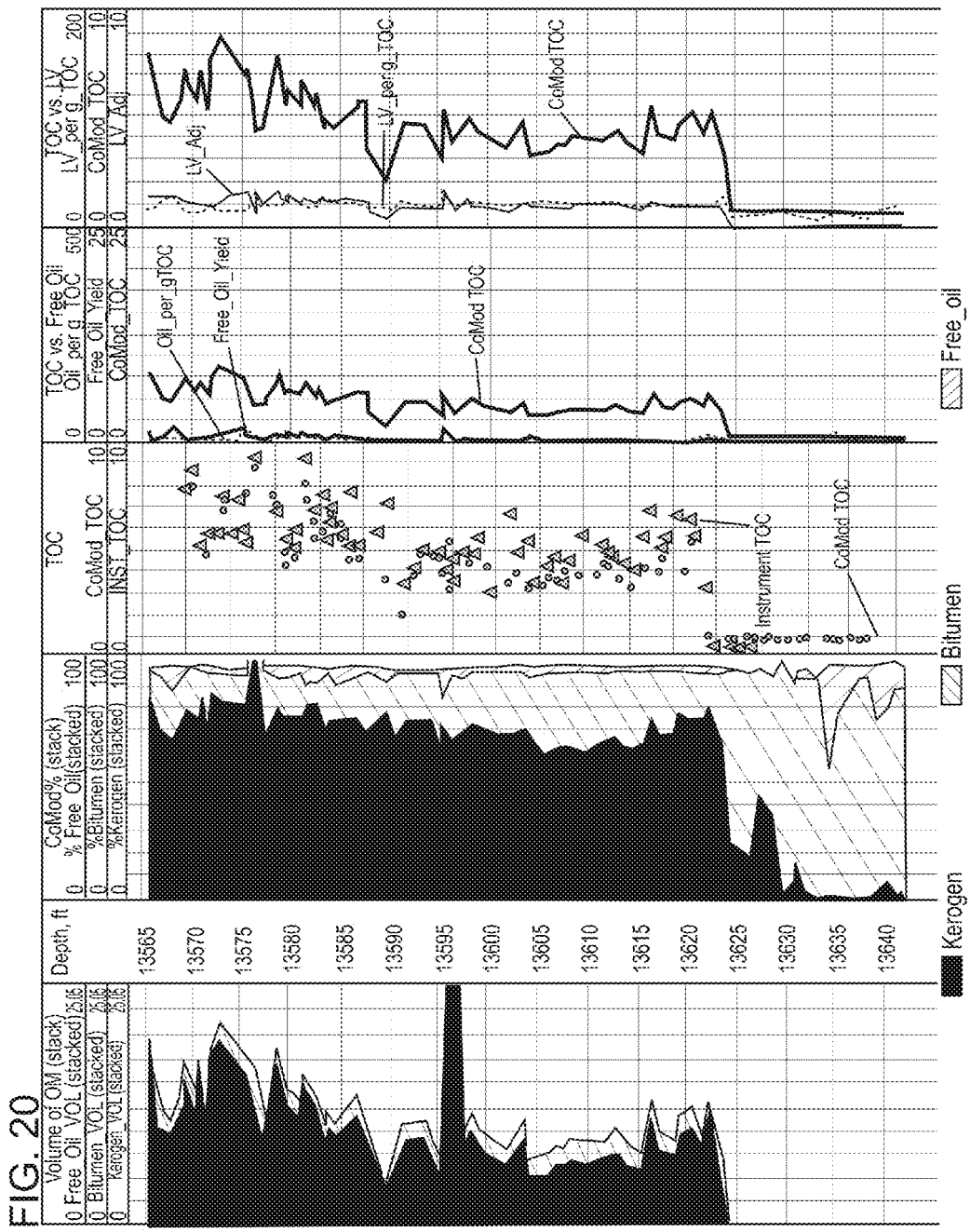
FIG. 20 is a composite log of the data obtained from the method of the invention that corresponds to FIG. 11 from the DBYT-1 well.

FIG. 20 is a composite log of the data provided from the method of the invention that corresponds to FIG. 11 from the DBYT-1 well. As can be readily observed, the results for the well as a whole are similar to the example for single samples. Most notably, in these plots is the lack of "Free Oil" end member in the MZLJ-29 well samples. Also, Tracks 4 & 5 that show the crossover effect for DBYT-1 when plotting TOC and "Free Oil" or TOC and LV, show no crossover for the MZLJ-29 well. Lastly, well tests and stimulation of the section shown for the MZLJ-29 well did not recover any hydrocarbon, whereas, the DBYT-1 well was able to flow oil. Thus, the subject methods are able to predict well performance in cases where the standard industry method provides equivocal information.

The above description is intended to be illustrative and not exhaustive. This description will suggest many modifications, variations, and alternatives to those of ordinary skill in this art that are within the scope of the present invention. Those familiar with the art may recognize other equivalents to the specific embodiments described above. Accordingly, the scope of protection is to be determined by the claims that follow.

What is claimed is:

1. A method of estimating the total organic carbon (TOC) content in a sample of reservoir rock from a known depth taken from a specific oil field, the sample containing a plurality of distinguishable end member (EM) components that can include oil, bitumen, soluble tar, pyrobitumen, kerogen, coal, drilling mud additives such as lubricants, mud stabilizers, lost circulation material, and other carbon-containing contaminants, the improvement comprising:
   a. determining a set of local end members for compositional modeling;
   b. applying compositional modeling to determine the relative proportion of each of the local end members in the sample;
   c. recording the values of the percent of total yield of each end member in the sample;
   d. obtaining parameters for the total hydrogen index ($THI_{OM}$), the ratio of organic matter-to-pyrolizable hydrocarbons ($OM/HC_{py}$), the ratio of hydrogen to carbon in the organic matter ($H/C_{OM}$), the percent of Nitrogen, Oxygen, and Sulfur in the organic matter ($NOS_x\%$), and the weight of Hydrogen in the organic matter (Wt % $H_{om}$),
   e. applying compositional modeling to determine the hydrocarbon yield ($Yield_{EMx}$) that is attributable to each EM in the sample;
   f. determining the weight of organic matter (OM) represented by the hydrocarbon yield in accordance with the following:

$$EM_x \text{ Weight OM} = Yield_{EMx} \times OM/HC_{Pyx}$$

where $HC_{Pyx}$ is a pyrolizable hydrocarbon end member;
   g. determining the weight of elemental nitrogen, sulfur and oxygen in accordance with the following:

$$EM_x \text{ WeightNSO} = NSO_x\% \times EM_x \text{ Weight OM};$$

h. determining weight of hydrogen for each end member in a sample by the equation:

$$EM_x \text{ WeightH} = Wt\% H_{OM} \times EM_x \text{ Weight OM};$$

i. calculating the total organic carbon for the end member ($TOC_{EMx}$) as follows:

$$TOC_{EMx} = EM_x \text{ Weight OM} - EM_x \text{ Weight NSOs} - EM_x \text{ Weight H};$$

j. summing the TOC for each end member and the inert carbon present in the formation to get the reconstructed total organic carbon ($TOC_{RCN}$ or $TOC_{CoMod}$) as follows:

$$TOC_{RCN} = TOC_{EM1} + TOC_{EM2} \ldots TOC_{EMx} + TOC_{inert}$$

2. The method of claim 1 in which the set of local end members is determined by (i) analyzing the sample to determine the presence of each end member or (ii) selecting the end members based on pre-existing analytical results from rock samples obtained from one or more comparable zones of interest in adjacent wells in the reservoir rock formation.

3. The method of claim 1 which includes the further preliminary steps of collecting a plurality of samples from the same depth, identifying one or more samples that exhibit a uniformity in the content of at least one end member, selecting one sample having substantially uniform end member content, and subjecting that sample to steps (b) through (j).

4. The method of claim 1 which further includes:
   k. selecting a plurality of samples from different intervals in the reservoir rock formation;
   l. repeating steps (b) through (j) on each of the samples;
   m. displaying the results in a graphic and/or tabular form for visual analysis by a user.

5. The method of claim 4 in which the results are displayed in tabular form for each of the plurality of samples and the table includes the estimated TOC and depth from which the sample was obtained, and related data selected from the group consisting of free oil, bitumen, kerogen and inert organic matter.

6. The method of claim 4 in which the TOC data are displayed graphically in stack form corresponding to the depth of the respective samples and the display includes volume of organic matter, % of kerogen, TOC vs free oil and TOC vs light volatiles (LV) as measured by the Pyrolytic Oil-Productivity Index (POPI) pyrolysis method.

7. A method for the reconstruction of total organic carbon content from compositional modeling analysis, the method comprising:
   a. collecting a plurality of samples typical of unconventional oil reservoirs and source rocks;
   b. performing pyrolysis by the Pyrolytic Oil-Productivity Index (POPI) pyrolysis method;
   c. obtaining and reviewing preexisting pyrolysis data for comparative samples obtained from a nearby well and the same reservoir to assess the likely end-member components that appear to be present in those comparative samples;
   d. selecting samples obtained in step (a) that appear to have a substantially uniform composition of an end-member, selected from the group of end members consisting of free oil, bitumen, kerogen such as appearing to be composed mostly of "free oil", bitumen, kerogen and contaminants;
   e. separating and moveable hydrocarbon component by extraction with a non-polar solvent, saving both the extract and extracted rock;
   f. separating and soluble tar from extracted rock by extraction with polar solvent, saving both extract and extracted rock;
   g. performing separation of residual organic matter on a portion of the polar solvent extracted rock by demineralization methods;
   h. analyzing all extracts and organic matter separations by elemental analysis to determine the percent of C, H, N, O, and S in each sample;
   i. analyzing all extracts, extracted rocks, and separated organic matter by pyrolysis-TOC analysis to determine THI;
   j. analyzing the pyrolysis data by applying compositional modeling;
   k. recording the value for the percentage of total yield for end-members in the group of samples;
   l. obtaining parameters for the total hydrogen index ($THI_{OM}$), the ratio of organic matter-to-pyrolizable hydrocarbons ($OM/HC_{py}$), the ratio of hydrogen-to-carbon in the organic matter ($H/C_{OM}$), the percent of Nitrogen, Oxygen, and Sulfur in the organic matter ($NOS_x\%$), and the weight of Hydrogen in the organic matter (Wt% $H_{OM}$);
   m. analyzing a plurality of samples from a well that has a source rock or unconventional reservoir where the reconstructed TOC values are needed;

n. applying compositional modeling to obtain the hydrocarbon yield that is attributable to each end member ($Yield_{EMx}$) in a group of samples from a source rock or unconventional reservoir;

o. determining the weight of organic matter represented by the hydrocarbon yield by applying the equation:

$EM_x$ Weight OM=YieldEMx×OM/$HC_{pyx}$;

p. determining the weight of elemental Nitrogen, Sulfur, and Oxygen by the equation:

$EM_x$ Weight NSOs=$NOS_x$%×$EM_x$ Weight OM;

q. determining weight of Hydrogen for each end member in a sample by the equation:

$EM_x$Weight H=Wt% $H_{OM}$×$EM_x$ Weight OM;

r. calculating the total organic carbon for the end member ($TOC_{EMx}$) as follows:

$TOC_{EMx}$=$EM_x$ Weight OM−$EM_x$ Weight NSOs−$EM_x$ Weight H; and s. summing the TOC for each end member and the inert carbon present in the formation to obtain the reconstructed total organic carbon ($TOC_{RCN}$ or $TOC_{CoMod}$) as follows:

$TOC_{RCN}$=$TOC_{EM1}$+$TOC_{EM2}$ . . . $TOC_{EMx}$+$TOC_{inert}$.

\* \* \* \* \*